(12) United States Patent
Shachar et al.

(10) Patent No.: US 9,310,363 B2
(45) Date of Patent: Apr. 12, 2016

(54) **METHOD AND APPARATUS FOR FORMING OF AN AUTOMATED SAMPLING DEVICE FOR THE DETECTION OF *SALMONELLA ENTERICA* UTILIZING AN ELECTROCHEMICAL APTAMER BIOSENSOR**

(75) Inventors: Yehoshua Shachar, Santa Monica, CA (US); Winston Wu, Alhambra, CA (US); Thomas Chen, La Canada, CA (US); Leslie Farkas, Ojai, CA (US); Brett Jordan, Los Angeles, CA (US); Paladin Luboff, Santa Monica, CA (US); Herwin Chan, Los Angeles, CA (US); Kyle Zimmerman, Los Angeles, CA (US)

(73) Assignee: Sensor-Kinesis Corporation, Los Angeles, CA (US)

( * ) Notice: Subject to any disclaimer, the term of this patent is extended or adjusted under 35 U.S.C. 154(b) by 1608 days.

(21) Appl. No.: 12/764,828

(22) Filed: Apr. 21, 2010

(65) Prior Publication Data

US 2011/0162979 A1    Jul. 7, 2011

Related U.S. Application Data

(63) Continuation-in-part of application No. 12/684,025, filed on Jan. 7, 2010.

(51) Int. Cl.
*C12Q 1/04* (2006.01)
*G01N 33/543* (2006.01)
*G01N 33/569* (2006.01)

(52) U.S. Cl.
CPC ...... *G01N 33/5438* (2013.01); *G01N 33/56916* (2013.01); *G01N 2333/255* (2013.01)

(58) Field of Classification Search
CPC ................................................ G01N 27/26
USPC ......... 506/13; 424/9.1; 435/6.11, 91.1, 91.31; 204/403.01; 205/777.5; 536/23.1
See application file for complete search history.

(56) References Cited

U.S. PATENT DOCUMENTS

| | | |
|---|---|---|
| 5,510,241 A | 4/1996 | Thorns |
| 5,582,981 A | 12/1996 | Toole et al. |
| 5,635,617 A | 6/1997 | Doran et al. |
| 5,712,170 A | 1/1998 | Kouvonen et al. |
| 5,840,867 A | 11/1998 | Toole et al. |
| 6,680,377 B1 | 1/2004 | Stanton et al. |
| 7,040,139 B2 * | 5/2006 | Sunshine ................. 73/23.2 |
| 2005/0136419 A1 * | 6/2005 | Lee ........................... 435/6 |
| 2005/0232747 A1 * | 10/2005 | Brackmann et al. ........ 414/803 |
| 2006/0181425 A1 * | 8/2006 | Crane et al. ................. 340/612 |
| 2006/0267570 A1 * | 11/2006 | Arkin .......................... 324/71.4 |
| 2007/0185680 A1 * | 8/2007 | Kambe et al. ............... 702/127 |
| 2007/0292941 A1 * | 12/2007 | Handique et al. ........ 435/288.7 |
| 2008/0200343 A1 * | 8/2008 | Clemens et al. ............. 506/9 |
| 2008/0254446 A1 | 10/2008 | Sode et al. |
| 2009/0058593 A1 * | 3/2009 | Breed ......................... 340/5.2 |
| 2009/0322510 A1 * | 12/2009 | Berger et al. ............. 340/539.1 |
| 2011/0053283 A1 * | 3/2011 | Hood et al. .................. 436/104 |

OTHER PUBLICATIONS

Zelada-Guillen et al., (Angewandte Chemie International Edition, 2009, vol. 48, pp. 7334-7337, "Immediate detection of living bacteria at ultralow concentrations using a carbon nanotube based potentiometric aptasensor").*
Brenner et al. (Journal of Clinical Microbiology, 2000, vol. 38, No. 7, pp. 2465-2467).*

* cited by examiner

*Primary Examiner* — Jane Zara
(74) *Attorney, Agent, or Firm* — Marcus C. Dawes; Daniel L. Dawes

(57) ABSTRACT

An aptamer-based solid-state electrochemical biosensor for label-free detection of *Salmonella enterica* serovars utilizing immobilized aptamers. The device is realized by forming a matrix array of parallel capacitors, thus allowing the realization of low-cost, portable, fully integrated devices. Protein-aptamer binding modulates the threshold voltage of a circuit, changing the impedance (capacitance) of the circuit. This circuit is further characterized by an electrode coded with a p-Si substrate, enhancing the affinity between the *Salmonella* outer membrane proteins (OMPs) and the aptamer. An aptamer embedded detection plate is configured within a testing lid device that fits a standard, commercially available polymer specimen jar. A sample is mixed with broth for incubation and cultivation of any present *Salmonella* bacteria to obtain acceptable concentration of the pathogen for testing. The information obtained can then be transmitted by wireless network.

7 Claims, 16 Drawing Sheets

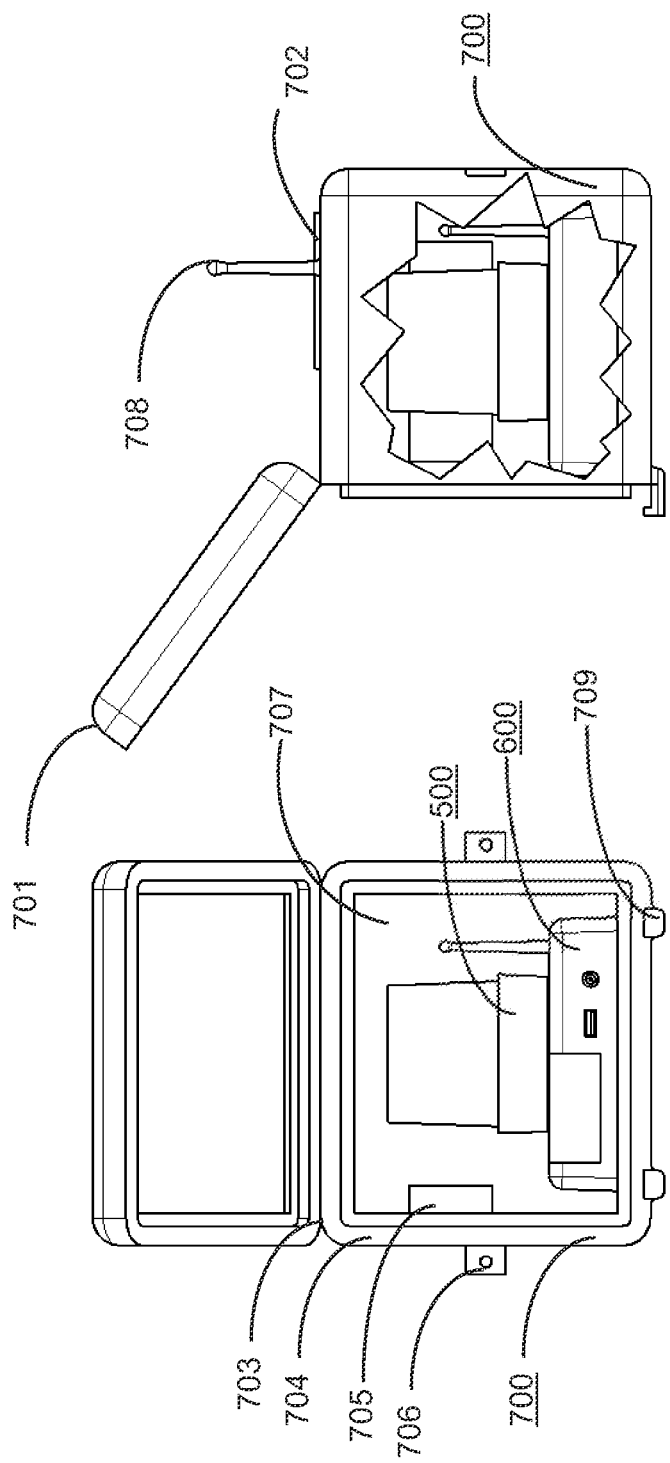

METHOD AND APPARATUS FOR FORMING OF AN AUTOMATED SAMPLING DEVICE FOR THE DETECTION OF *SALMONELLA ENTERICA* UTILIZING AN ELECTROCHEMICAL APTAMER BIOSENSOR

RELATED APPLICATIONS

The application is related to co-pending U.S. patent application Ser. No. 12/422,125, titled 'Method and Apparatus for Forming a Homeostatic Loop Employing an Aptamer Biosensor', filed Apr. 10, 2009.

BACKGROUND OF THE INVENTION

1. Field of the Invention

The invention relates to the field of chemical biosensors, specifically the use of electrochemical aptamer biosensors utilized in an automated in situ test for the presence of *Salmonella enterica* bacteria.

2. Description of the Prior Art

*Salmonella* is a genus of rod-shaped, gram-negative, non-spore forming, and predominantly motile enterobacteria. Salmonellae are a significant cause of food borne illness worldwide. Around 1.4 million cases of salmonellosis are reported annually in the US, with approximately 16,000 hospitalizations and 550 deaths. *Salmonella* alone is associated with 26% of all the food borne diarrheal cases leading to hospitalization. *Salmonella* bacteria are especially dangerous to humans because of their zoonotic nature, meaning that they have the ability to infect across several species.

Enteritis *Salmonella* (e.g. *Salmonella enterica*) can cause diarrhea, which usually does not require antibiotic treatment. But people at risk such as infants, HIV patients, small children, the elderly, and those with suppressed immunity can become seriously ill. Osteomyelitis may develop in children with sickle cell anemia who are infected with *Salmonella*. *Salmonella* bacteria are capable of causing typhoid fever. This infects over 16 million people worldwide each year, with 500,000 to 600,000 of these cases proving to be fatal, according to the World Health Organization.

*Salmonella* can survive for weeks outside a living body. Ultraviolet radiation and heat accelerate their demise; they perish after being heated to 55° C. (131° F.) for one hour, or to 60° C. (140° F.) for half an hour. They have been found in dried excrement after over 2.5 years. To protect the population from *Salmonella* infection, governments and other rule-making bodies have enacted many rules regarding the handling of food. For cooking at home, it is recommended that food be heated for at least ten minutes at 75° C. (167° F.) at the center of the food that is being prepared. *Salmonella* is not destroyed by freezing.

There have been many attempts to control the spread of *Salmonella* bacteria in the food supply. One method of this is to disseminate information on proper food handling and cooking techniques. This is done by a wide variety of rules and regulations regarding the production, shipping, and handling of food.

One aspect of food regulation is determining acceptable levels of *Salmonella* bacteria in food products. The USFDA has, for example, set an acceptable level for *Salmonella* in the water supply as not greater than 3CFU/4 gm. (www.fda.gov.)

Of particular concern is salmonellosis caused by multidrug resistant (MDR) strains such as *Salmonella enterica* serovar Typhimurium DT104 or *S. enterica* serovar Newport. Drug resistant strains are, by their nature, much more difficult to treat than other strains of *Salmonella*. They can be particularly devastating to at-risk groups, such as infants and the elderly. It is in the case of MDR strains of *Salmonella* especially that it is important to have accurate, easy to administer testing of food sources. In this way, the initial transmission of the pathogen to humans can be reduced or eliminated.

Because of the great need for accurate testing for the presence of *Salmonella*, there are many testing methods available today commercially. The USFDA has guidelines for testing (see USFDA *Setting a Risk Threshold for Enteric Diseases in Drinking Water*), as has the USDA (see *Salmonella* Testing). Testing is traditionally accomplished either through DNA based methods (e.g. GENE-TRAK Colorimetric, and TAQ-MAN by PE Applied Biosystems), through Immunoassay based methods (e.g. EIA Foss by Foss Electric), through immuno-latex aggulation based methods (e.g. Spectate by May & Baker Diagnostics Ltd.), and also sometimes through other biochemical methods such as a motility detection system (e.g. *Salmonella* Rapid Test by Oxoid).

These tests are widely used and accurate, but some can take many days to accomplish, and many of these tests are not highly automated, namely they all rely on the technician to determine the outcome of the test. Additionally, these tests are accomplished at a certain point of time, often by in-lab enrichment of the bacterial sample.

Aptamers are well known in the field for their ability to bind to specific substances. Nucleic acid based aptamers are highly stable also. Aptamer specificity is often determined utilizing the systematic evolution of ligands by exponential enrichment (SELEX) method. This allows for high specificity to a wide variety of molecules. Aptamers are now gaining use as markers and linkers to cells. Aptamers are able to bind to the outer membrane proteins of cells and therefore act as markers and binders to the cell. (Joshua K. Herr et al., *Aptamer-Conjugated Nanoparticles for Selective Collection and Detection of Cancer Cells*, Analytical Chemistry, Vol. 78, No. 9, pp. 2918-2924, May 2006.)

Utilizing aptamer binding to *Salmonella enterica* has undergone proof of principle testing under Raghavendra Joshi et al. (Raghavendra Joshi et al., *Selection, characterization, and application of DNA aptamers for the capture and detection of Salmonella enterica serovars*, Molecular and Cellular Probes, Vol. 23, pp. 20-28, 2009). In those experiments, two highly specific 40-mer single DNA strand *Salmonella enterica* aptamers were discovered.

By utilizing the discovered two sequenced aptamers, Joshi et al, were able to utilize aptamer-infused magnetic particles to separate and concentrate *Salmonella enterica* bacteria in a sample, and thereby detect seven distinct serotypes of *Salmonella enterica*, with a detection sensitivity of about 10 CFU/gm.

U.S. Pat. No. 5,510,241 ("Thorns") discloses a testing system for *Salmonella* bacteria, but does so utilizing monoclonal antibodies.

U.S. Pat. No. 5,582,981 ("Toole et al.") discloses use of aptamer technology for binding to specific substances, but utilizes polymerase chain reaction. PCR testing requires a laboratory environment and a trained technician.

U.S. Pat. No. 5,635,617 ("Doran et al.") discloses a specific target gene and protein of *Salmonella* bacteria; however, it does not apply this to a procedure for automated testing for the pathogen in food.

U.S. Pat. No. 5,712,17 ("Kouvonen et al.") discloses a rapid immunoassay test strip that could be utilized for testing for pathogens, but does not disclose a way to do so in an automated way, and Kouvonen's method further requires a trained technician to accomplish the testing.

U.S. Pat. No. 5,840,867 ("Toole et al.") discloses several specific aptamer sequences that may be utilized for targeting. However, it does not disclose a specific method for their use, nor does it disclose an aptamer specific to *Salmonella enterica* outer membrane proteins.

U.S. Pat. No. 6,680,377 B1 ("Stanton et al.") discloses the composition of aptamers as beacons. Because this is not an electrochemical feedback system, it requires trained lab personnel and lab equipment. Also, this piece of prior art does not disclose a detection system for *Salmonella enterica*.

What is needed in the field is a highly automated, accurate system that can be used outside of the laboratory environment, specifically at "Points-of-Inspection" such as ports, border check-points, and weighing stations along the normal paths of commerce by lay practitioners to accurately test for the presence of *Salmonella* in food samples in situ.

BRIEF SUMMARY OF THE INVENTION

The disclosed invention and method provides a highly automated system for testing for *Salmonella enterica* bacteria. These testing procedures are highly automated so as to allow minimal training to be required in order to carry out the examination. Further, a method is disclosed herein for testing that allows results to be wirelessly transmitted while goods are in transit, allowing for quick processing at loading and unloading locations.

The device is utilized first by taking a pre-set amount of commercially available broth (such as BHI broth) that is appropriate for the standard commercially available specimen cup size being used. Next, a small sample of the item to be tested (e.g. a piece of chicken) is placed into the cup using commercially available sterilized tablespoons, scissors, forceps, knives, glass stirring rods, pipettes, petri dishes, test tubes, bent glass rods ("hockey sticks") as needed. Next, the specimen cup container lid (with aptamer biosensor array built in) is placed securely on the top of the specimen cup, and the cup is shaken vigorously for a short period of time to mix the contents and broth. Finally, the cup is placed top-side-down onto the base station unit, with the USB ports in the lid and the base station securely connected. The remainder of the testing process is accomplished without the aid of human hands.

Following the preparation of the sample described above, the base station allows time for the incubation of the *Salmonella* sample in broth to detectable levels. The amount of incubation time is determined by the ambient temperature. A temperature sensor is built into the PCB in the lid, thereby allowing accurate measurement of the temperature in the sample. Based upon calculations found in prior art (Vijay K. Juneja et al., *Modeling the effect of temperature on growth of Salmonella in chicken*, Food Microbiology, Vol. 24, pp. 328-335, 2007), if the temperature of an incubation cycle is known, the amount of time needed for a proper incubation cycle can be determined with great accuracy. In this way it is not necessary to artificially control the temperature of the incubation of the *Salmonella enterica* bacteria during testing.

Once the proper incubation period has been completed, a novel biochemical aptamer-based biosensor is utilized to measure for the presence and quantity of *Salmonella enterica* bacteria. The invention utilizes aptamer binding DNA strands immobilized onto a capacitance array to accomplish the testing process. Immobilized aptamers have a high affinity and specificity for binding to the outer membrane proteins (OMPs) of the *Salmonella* bacteria. Capacitance plates form a 'comb' like structure to create a sensor array, where the two facing sides of the comb 'teeth' create the positive and negative interfaces of the capacitance circuit. When a source being sampled contains *Salmonella enterica* bacteria, the immobilized aptamer binds to the *Salmonella* bacteria and traps it between the capacitance plates. The capacitance between plates is measured. Because the presence of *Salmonella enterica* bacteria changes the capacitance between the plates, measuring the capacitance allows for detection of the level *Salmonella* bacteria in the sample. This method creates an electrochemical biosensor that is capable of testing for the presence of *Salmonella enterica* bacteria from a given sample.

The device is formed from a standard polymer specimen cup attached to a specialized testing device lid. The testing device lid utilizes *Salmonella enterica* specific aptamers in a microfluidics electrochemical sensor array, allowing for testing results to be timed and interpreted by pre-programmed computer software. Use of microfluidic technology increases the sensitivity of the aptamer sensor array.

The device utilizes aptamers that specifically bind to the outer membrane proteins of the *Salmonella enterica* bacteria. The aptamers utilized in this invention are short (40-mer) DNA nucleotide sequences which are molecule specific because of their predictable 3 dimensional folding characteristics. The aptamer folds with high specificity onto the outer membrane proteins specific to *Salmonella enterica*, thereby trapping the *Salmonella* bacteria. Once the *Salmonella* bacteria are trapped between the capacitance plates, the capacitance of the medium is tested using the built-in solid state circuitry. Based upon change in the capacitance of the medium between the capacitance plates, the concentration of *Salmonella* bacteria can be tested. This process is explained in greater detail below.

The testing device lid employs a standard Universal Serial Bus (USB) connector built into the external surface of the lid. Internally, the lid features an aptamer sensor array which optionally features a built-in micropump to ensure proper fluid circulation during testing. The aptamer sensor array is built into a printed circuit board (PCB) that allows for control of the sensor array. The PCB also includes a temperature sensor. Temperature sensor readings are periodically tracked by a software algorithm to accurately predict the state of the testing process.

The base of the device utilizes a USB connection to connect to the testing device lid. Embodied in the base station of the invention is a wireless antenna for communication of testing results to Wi-Fi computer networks often available at shipping yards. There is an additional USB connection on the front of the device, allowing the base station to be programmed by a standard desktop computer with appropriate compatible software. Further, this USB connection may be utilized to connect and upgrade the device, providing an additional externalized battery supply for long voyages, or by up-linking to a cellular phone or sat-phone capable device to provide worldwide network access to the testing unit.

The base of the device utilizes a standard Liquid Crystal Display (LCD) screen to output visually the state and results of the testing procedure without the need to connect to a standard personal computer. A PCB board features a central processing unit, flash memory for storage, and other components needed to provide proper running protocols for the device. The base station also utilizes standard rechargeable C sized or like batteries as a power source when needed. A plug-in device to recharge the batteries is located on the front of the base station adjacent to the LCD screen.

The device is utilized by adding a small amount of commercially available broth (such as BHI broth) to the sterile standard specimen cup, removing the optional plastic covering protecting the aptamer sensor plate, adding a sample of the food to be tested, and then subsequently firmly attaching the testing device lid to the specimen cup. The cup and lid is then turned upside-down and placed in this orientation upon the base station. The base station utilizes an always on real-time clock. Based upon the ambient temperature and time, the protocols designed into the base station will analyze the sample at the appropriate times to ensure accurate measure.

After the broth is added to the specimen cup, the sample is added. Incubation is accomplished at ambient temperature to increase the bacterial load to testable levels. The programming of the unit allows for independent calculation of the length needed to test the Salmonella bacteria load in the sample.

Accordingly, the present invention may have one or more of the following advantages:

It is therefore an embodiment of the invention to allow for a simple and highly automated procedure for testing for Salmonella enterica bacteria by utilizing a standard specimen cup with a specially designed testing device lid.

It is a further embodiment of the invention that the calculation of the testing for Salmonella enterica bacterial be accomplished in a base station device incorporating temperature and aptamer biosensor data from the cup, and to provide an accurate measurement of the progress of the testing procedure.

It is yet another embodiment of the invention that the base station device is enabled with wireless capability to allow in situ inspection of data from testing.

It is another embodiment of the invention that it may be powered by battery, by DC current from a truck or car, or by AC current from a wall socket or other source.

In a further embodiment of the invention, once the sampling process is completed, the device may be attached externally to a shipping container in a case. This case may be bolted, welded, or magnetically attached to the outside of a container.

It is another embodiment of the invention that the test may be started at the first point of shipment, and that the testing unit may follow that cargo container. In this way, regardless of the testing time needed, the testing time overlaps with the travel time of the cargo. Utilizing this method, many shipments would have completed their test for *Salmonella* before they reach their destination, thereby making the authorization of the shipment more efficient.

It is another embodiment of the invention that data could be harvested from the automated testing device at wireless access points located at Points-of-Inspection, providing real-time access to the data. One example of the use of this for practical purposes follows. A trucker hauling spinach with the device analyzing a sample during transit could drive through a weigh station where there is Wi-Fi access. At that time, if the sample is deemed tainted, the central office for the shipment company could be notified via the internet, and the central office would notify the trucker to take the tainted spinach to an alternative site because it is no longer fit for human consumption. Connection between the analyzer unit and the central office could be further heightened by connecting the base station to a cell phone or satellite phone connection via the USB port on the front of the base station.

It is finally an embodiment of the invention that data is collected over time, allowing for aggregation of *Salmonella enterica* bacterial growth to be recorded over the time of each shipment, allowing for more detailed studies to be performed regarding food spoilage.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is an external perspective view of the cup and base station of the apparatus.

FIG. 2A is an external view of the specimen cup and testing lid of the device showing the docking hole and USB docking port connection between the specimen cup lid and the base.

FIG. 2B is an alternative partially cut-away external view of the of the specimen cup, highlighting the electrochemical aptamer testing site placement upon inside of the lid device.

FIG. 2C is a partially cut-away side view of the internal components of the testing lid device for the specimen cup, highlighting the aptamer sensor plate attached to the printed circuit board (PCB), and the USB connection.

FIG. 2D is a perspective view of the printed circuit board with attached aptamer electrochemical sensor plate, present within the testing lid device of the invention. The temperature sensing chip is visible on the PCB.

FIG. 2E depicts the reverse side of the printed circuit board shown in FIG. 2D and an array of electrodes coded with *Salmonella* sensors forming a series of grooved capacitive plates disposed thereon.

FIG. 3A is a partially cut-away perspective view of the base unit, with internal visible components including the PCB, wireless antennae, output display screen, and data connection port.

FIG. 3B is a frontal transparent view of a weatherproof enclosure utilized to house the device on the external surface of a shipping container. The additional battery pack and externalized antennae are also shown.

FIG. 3C is a partially cut-away side view of the enclosure seen in FIG. 3B.

FIG. 4A is a magnified cross sectional view of the capacitive arrangement of the *Salmonella* detector shown in FIG. 2E.

FIG. 4B is a graphic depiction of the *Salmonella* sensor hybridization element.

FIG. 4C is a graphic depiction of the *Salmonella* sensor hybridization element, including a depiction of the structure and nucleotide sequence.

FIG. 5 is a cross sectional view of the capacitive arrangement shown in FIG. 4A including a schematic representation of the electrical detection module.

FIG. 6 is a schematic representation of the preferred embodiment of the invention depicting one cell of an equivalent electrode-electrolyte node from the capacitor array.

FIG. 7 is a schematic representation of the capacitor matrix array depicting the equivalent circuit to that of the circuit shown in FIG. 6.

FIG. 8 is a block diagram of the temperature sensor which is a component of the lid assembly of the unit shown in FIG. 1.

FIG. 9 is a schematic block diagram of the computations performed by the central processing unit (CPU) on the printed circuit board in the base of the device shown in FIG. 3A.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DEFINITIONS

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

"Serovar" or "Serotype" is the short form of referring to the serological variants of *Salmonella* bacteria, and is a way to distinguish between distinct types of *Salmonella* bacteria. The particular serovar of a *Salmonella* strain refers to the individual classification of that bacteria within the genus, as based upon cell membrane antigens. Serotyping often plays an essential role in determining species and subspecies. The *Salmonella* genus of bacteria, for example, has been determined to have over 4400 serotypes, including *Salmonella enterica* serovar Typhimurium, *S. enterica* serovar Typhi, and *S. enterica* serovar Dublin.

"BHI broth" refers to for Brain Heart Infusion broth, which is a general-purpose liquid medium used in the cultivation of fastidious and nonfastidious microorganisms, including aerobic and anaerobic bacteria, from a variety of clinical and nonclinical materials. The broth medium may be supplemented with Sodium Chloride. BHI Broth is used for the cultivation of a wide variety of microorganisms, including bacteria, yeasts and molds.

"CFU" is an abbreviation of colony-forming units, which are a form of measurement of live bacterial growth.

In microbiology, the measure of colony-forming unit (CFU or cfu) expresses the quantum of viable bacterial or fungal numbers. Unlike direct microscopic counts (where all dead and living cells are counted) CFU measures viable cells. Results are given either as CFU/mL (colony-forming units per milliliter) for liquids, or CFU/g (colony-forming units per gram) for solids. Because this invention utilizes a liquid broth to provide an incubation medium, the measurement of CFU/mL is utilized for admeasurement of *Salmonella enterica* density.

Pathogen as used herein refers to a biological agent that causes disease or illness to its host.

Electrochemistry as used herein refers to a branch of chemistry that studies chemical reactions which take place in a solution at the interface of an electron conductor (a metal or a semiconductor) and an ionic conductor (the electrolyte), and which involve electron transfer between the electrode and the electrolyte or species in solution.

Aptamer as used herein refers to oligonucleic acids or peptide molecules that bind to a specific target molecule.

*Salmonella* as used herein refers to a genus of rod-shaped, predominantly motile, enterobacteria. It can be found in animal, human, and non-living habitats.

Pilus (plural Pili) as used herein refers to a hair-like appendage found on the surface of many bacteria. The terms pilus and fimbria are often used interchangeably, although some researchers reserve the term pilus for the appendage required for bacterial conjugation. All pili are primarily composed of oligomeric pilin proteins.

IVB Pili as used herein refers to bacterial pili that generate motive forces.

"Mfold" refers to RNA and DNA predictive folding package software developed by Dr. Michael Zuker, currently hosted by Rensselaer Polytechnic Institute, Troy, N.Y. (See http://mfold.bioinfo.rpi.edu/). Mfold software provides secondary structure prediction metrics for RNA and DNA molecules. Mfold's analysis relies primarily upon by thermodynamic methods.

The "primary structure" of a molecule is defined in biochemistry as the exact specification of its atomic composition and the chemical bonds connecting those atoms.

"Secondary structure" is a term defined in biochemistry and structural biology as the general three-dimensional form of local segments of biopolymers such as proteins and nucleic acids (DNA/RNA).

Monocytic-Cell as used herein refers to a type of white blood cell, part of the human body's immune system.

Electrophoresis as used herein refers to the motion of dispersed particles relative to a fluid under the influence of a spatially uniform electric field.

Plasmon as used herein refers to a quantum of plasma oscillation. The plasmon is a quasiparticle resulting from the quantization of plasma oscillations just as photons and phonons are quantizations of light and sound waves, respectively.

"Surface modification" as used herein refer to the process of detailed by Y. Han et al., 2006 which describes preparing the $SiO_2$ surface, as it is cleaned with MeOH/HCl (1/1) for 30 minutes at room temperature, rinsed with ultra pure water (Milli-Q Gradient A10 18.2 MΩ, and dried with Argon. In the next step, the surface is modified with $NH_2$ groups by a silanization step with 3-aminopropyltriethoxysilane (APTES) either in the gas phase. For gas-phase silanization, the chips are placed in a dessicator containing a few drops of silane. The desiccator is sealed and heated above 100° C., and the chips were left to react for 1-2 hours under a low pressure (~1 mbar) with the silane vapor. This technique employs biocompatible scaffolds provide viable alternatives forming the prosthetic materials for adhesion. The use of self assembled peptide amphiphile nanofiber coated scaffold to grow the linker, is advantageous because of its high surface area, which permits a large number of sites for the succinic anhydride, adhesion and growth. (Succinic anhydride, also called dihydro-2,5-furandione, is an organic compound with the molecular formula $C_4H_4O_3$.) The fibrous nature of the coating allows the linker, to penetrate the surface by diffusion, and the matrices have sufficient surface area and exposure to the linker. The linker, is further combined with an amino-silanization. (The surface of a quartz or glass wafer ($SiO_2$ 14) is treated with different aminosilanes in solution where surface density increased sharply with the reaction time and produced the multilayer.) The amino-silanization, scaffolds provide viable alternatives forming the prosthetic materials for adhesion to the $SiO_2$ insulator surface.

"Aptamer immobilization" as used herein refers to the process detailed by Hyun-Seung Lee et al., 2009, which describes immobilization, whereby a *Salmonella* DNA aptamers named above are dissolved in phosphate buffer (PB, 200 mM, pH 8) to prepare aptamer solution at a concentration of 20 mM. Each vial is incubated at room temperature for 4 hours. After that, aptamer solution (500 μL) is added and incubated at pH 7.5 and room temperature. The resulting substrates are washed with phosphate buffer saline (PBS) and water in a sequential manner. Finally, the substrates are air-dried and the immobilization is analyzed by atomic force microscopy (AFM), indicating an average of ~3 nm increase of surface thickness due to the immobilization of *Salmonella enterica* aptamers. Aptamer packing techniques are further described by Hwa Sung Lee et al. in *Effect of the Phase States of Self-Assembled Monolayers on Pentacene Growth and Thin-Film Transistor Characteristics* (J. Am. Chem. Soc., Vol. 130, No. 32, pp. 10556-10564, July 2008.) Additionally, Ryan J. White et al. have published research on aptamer density for detection of target molecules, finding that optimal aptamer packing density varies with particular target substances, and that higher-density aptamer probes are not always optimal for detection. (*Optimization of Electrochemical Aptamer-Based Sensors via Optimization of Probe Packing Density and Surface Chemistry*, Langmuir, Vol. 24, pp. 10513-10518, 2008.) Specifically, extrapolating from the principles shown in the White paper, aptamer probe packing density for *Salmonella* outer membrane proteins would be initially produced in the range of $1.2 \times 10^{11}$ to $4.4 \times 10^{12}$ molecules/cm$^2$. Other packing densities may be utilized without deviating from the spirit and scope of this invention, should they be found to be additionally optimal in detection and attachment of *Salmonella enterica* bacteria to the aptamer sensor plates.

The concept of using single-stranded nucleic acids (aptamers) as affinity molecules for protein binding was initially described in 1990 (Ellington and Szostak 1990, 1992; Tuerk and Gold 1990), and is based on the ability of short sequences to fold, in the presence of a target, into unique, three-dimensional structures that bind the target with high affinity and specificity. Eugene W. M Ng et al., 2006, describes that aptamers are oligonucleotide ligands that are selected for high-affinity binding to molecular targets.

"Fabrication of silicon insulator surface" as used herein refer to the process detailed by Hyun-Seung Lee et al., 2009, which describes a layer of Au (100 μm) deposited to form the interleaved array of electrodes 103, inside an insulating enclosure 17. Silicon crystal for p-doping 15 is grown on the Au conductor surface 16, with a constant flow of SiH$_4$ precursor at 530° C. under the gas pressure of 50 Torr. During this process, silicon crystals are in situ doped with B$_2$H$_6$ as p-dopants at the relative pressure ratio of SiH$_4$:B$_2$H$_6$ to be $10:1 \times 10^{-3}$. The flow of SiH$_4$ is continued but B$_2$H$_6$ is stopped when the p-substrate 15, reaches 1 μm. After the additional Si layer reaches 10 nm, the flow of SiH$_4$ is stopped; the temperature is raised to 820° C. and gas chamber is opened to the atmospheric pressure, allowing oxidation in the dry atmosphere to form the SiO$_2$ insulation layer.

"Capture reagent" as used herein, is a molecule or compound capable of binding the target analyte or target reagent, which can be directly or indirectly attached to a substantially solid material. The capture agent can be any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte" as used herein, is the substance to be detected in the test sample using the present invention. The analyte can be any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof: The target analyte can include a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances.

"Target analyte-analog" as used herein, refers to a substance which cross reacts with an analyte capture reagent although it may do so to a greater or lesser extent than does the target analyte itself. The target analyte-analog can include a modified target analyte as well as a fragmented or synthetic portion of the target analyte molecule so long as the target analyte analog has at least one epitomic site in common with the target analyte of interest.

"Test sample" as used herein, means the electrolyte solution containing the target analyte to be detected and assayed using the present invention. The test sample can contain other components besides the target analyte, can have the physical attributes of a liquid, or a gas, and can be of any size or volume, including for example, a moving stream of liquid. The test sample can contain any substances other than the target analyte as long as the other substances do not interfere with the binding of the target analyte with the capture reagent or the specific binding of the first binding member to the second binding member. Examples of test samples include, but are not limited to: Serum, plasma, sputum, seminal fluid, urine, other body fluids, and environmental samples such as ground water or waste water, soil extracts, air and pesticide residues.

"Methods and reagents" used by authors for the purpose of analysis and testing of the proposed apparatus are based on information provided by Hyun-Seung Lee et al., 2009 paper. The following reagents were used without further purification for the propose of identifying the method: 3-Aminopropyl diethoxysilane (APDES), succinic anhydride (SA), sodium carbonate (SC), phosphate buffered saline (PBS) tablet, sodium dodecylsulfate (SDS), 1-ethyl-3-[3-(dimethylamino) propyl]carbodiimide (EDC), N-hydroxysulfo succinimide (sulfo-NHS), sodium hydroxide (NaOH), sodium chloride (NaCl) (Sigma-Aldrich Co. St. Louis, Mo.).

The "SELEX" process is used by this invention to mean a technique for screening a very large library of oligonucleotides with random sequences by iterative cycles of selection and amplification.

"Effective sensor geometry" is used by this invention to mean the physical geometry $G_x$ of the biosensor and the arrangement of its sensing structures that maximize the sensing area with minimum volume. The capacitance due to the sensor geometry $C_{geometry}$ is described in Equation 1 using the dielectric ($\in_r$) as a variable that correlates with target analyte concentration in the test sample.

$$C_{geometry} = \varepsilon_r \varepsilon_0 \frac{A}{d} \tag{1}$$

Where $\in_r$ is the combined relative permittivity (dielectric constant) of the medium consisting of *Salmonella* bacteria, bodily fluid, Succinic anhydride linker, Amino hybridization substance, SiO$_2$ insulator, and p-Si substrate; $\in_0$ is the permittivity of the free space ($8.854\times10^{-12}$ F/m); A is the total area of electrode plates with width, and length; and d is the separation between the plates. The values of A and d are chosen so that the change in capacitance can be effectively measured with the following capacitance measurement technique.

For example, with the cross sectional area ($d_{cap} \times W_{cap}$) of the biosensor is approximately 1 cm×1 cm, which is broken into pairs of electrode plates arranged in a comb-like pattern, with rows of electrode plates tied to form two sets of plates. In an alternate embodiment, a digitated fingers pattern may be utilized in the structure of the electrode plate, creating a longer single fluid path. Following the insulator fabrication process described above, the combined thickness of one sensor plate is 102.02 μm (the sum of the thicknesses of electrode, two layers of p-substrate, and two layers of insulator). With the plate area of 1 cm² providing capacitance of around 10 uF, the size of the plates A and the distance between the plates d can be adjusted to meet the requirements of the detection circuit. The only variable in Equation 1 is the combined dielectric constant $\in_r$ that changes with *Salmonella* bacteria molecule hybridization with the surface.

The "Measurement technique" of the electrochemical cell is based on said sensing principle of a variable capacitor cell, where the dielectric ($\in_r$) of the electrode/solution interface model is the variable. In this model, the *Salmonella* bacteria outer membrane protein, *Salmonella enterica* aptamer, introduces additional insulating layers, between electrode and solution, resulting in a measurable change in capacitive component of the interface model. The charge-based capacitance measurement (CBCM) technique can measure this change in capacitive component of the electrode-solution interface impedance. The measurement principle of this CBCM technique is to charge and discharge the electrochemical cell at an appropriate frequency, and measure its equivalent capacitance from the average current in half-period, noted in Equation 2.

$$I_{avg} = \frac{\Delta Q}{T/2} = \frac{C\Delta V}{T/2} = 2C\Delta V f \qquad (2)$$

The variables ΔV and f are known and $I_{avg}$ can be measured. This measurement technique consists of two separate circuits. The Op Amp voltage follower increases the input impedance of the electrochemical cell so that the cell can be driven by a near perfect square wave, from a digital output signal line from a microcontroller. The frequency (f) of the square wave is chosen as the maximum frequency that completely charges and discharges the capacitor in the electrochemical cell in the half period. The second part converts $I_{avg}$, into voltage value with a known resistor value $R_1$, and amplified with an Op-Amp. $V_1$, at the output of the Op Amp, can be calculated as shown in Equation 3.

$$V_1 = C_{cell} R_1 \frac{dV_{in}}{dt} \qquad (3)$$

An Op Amp integration circuit converts the transient voltage values, into a square wave, as shown in Equation 4.

$$V_{out} = -\frac{1}{C_2} \int \frac{V_1}{R_2} dt \qquad (4)$$

Substituting Equation 2 into 3, the output of the above, as a function of its input can be calculated as shown in Equation 5 leading to Equation 6.

$$V_{out} = -\frac{1}{C_2 R_2} \int -C_{cell} R_1 \frac{dV_{in}}{dt} dt \qquad (5)$$

$$V_{out} = \frac{C_{cell} R_1}{C_2 R_2} V_{in} \qquad (6)$$

The output voltage, which is sampled by an ADC, is proportional to the value of $C_{cell}$.

Detailed Description of The Preferred Embodiments

The disclosed invention and method provides a highly automated system for testing for *Salmonella enterica* bacteria (2).

FIG. 1 shows an externalized view of the entire testing apparatus as a whole. A base station unit (600) utilizes a built-in LCD (602) for display of data. Examples of data shown would be progress of testing, current temperature, average temperature, current power level of the batteries, time to finishing of testing, and other such information. FIG. 1 exhibits a wireless antenna (601) coupled to the base station (600) for data communication over various frequencies as determined advantageous, a standard USB connection (603) disposed on the base station (600) for data and power transfer to an externalized programming device such as a personal computer (not shown), and external power supply connector (604) also disposed on the base station (600) for power which can be utilized from an AC or DC power source. Wireless communication is envisioned in a variety of frequency spectra, including the standard Wi-Fi 801.11b standard, which generally operates in the 2.4 GHz to 2.4835 GHz frequency range. In an alternative embodiment, the wireless antenna (601) could also be used to operate on standard international cellular phone frequencies, allowing for a wider area of wireless transmission. An additional externalized battery (705), as seen in FIG. 3Bm can be connected via the power port (604) or via the USB port (603) to extend the power cycle of the device.

Figure 2A:
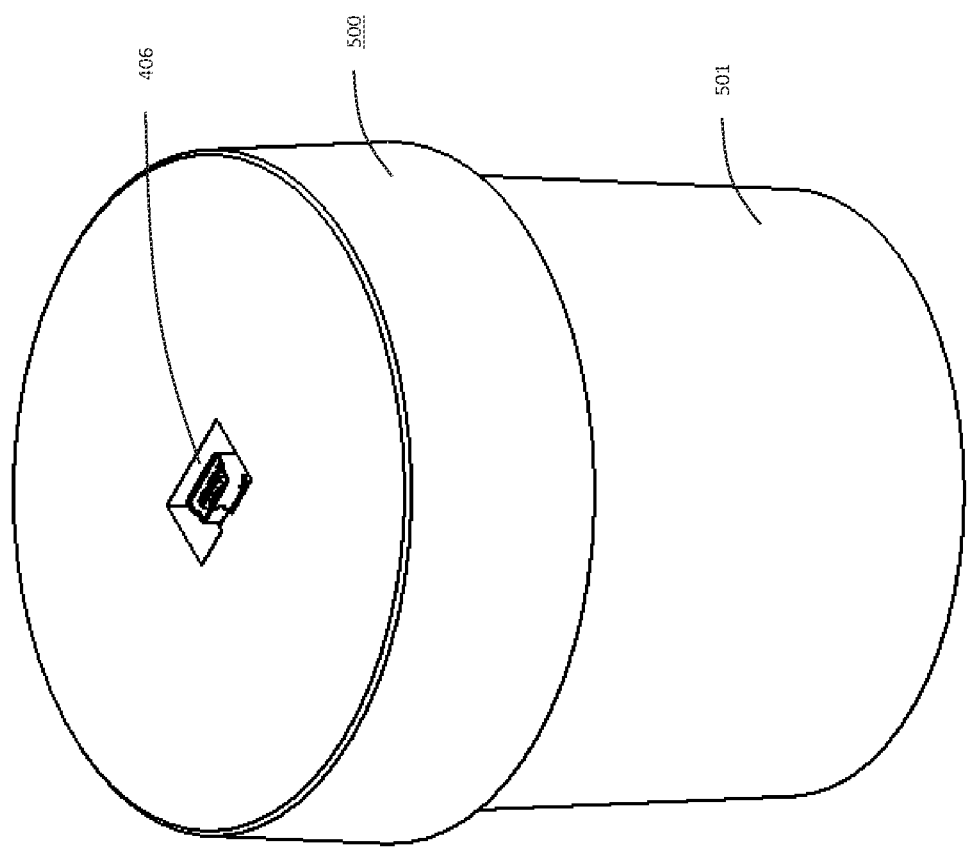
FIG. 2A depicts a testing device specimen cup (501) and lid (500). A USB communication port (406) disposed within the lid (500) that couples the lid (500) to the base station (600) can also be seen.
Figure 2B:
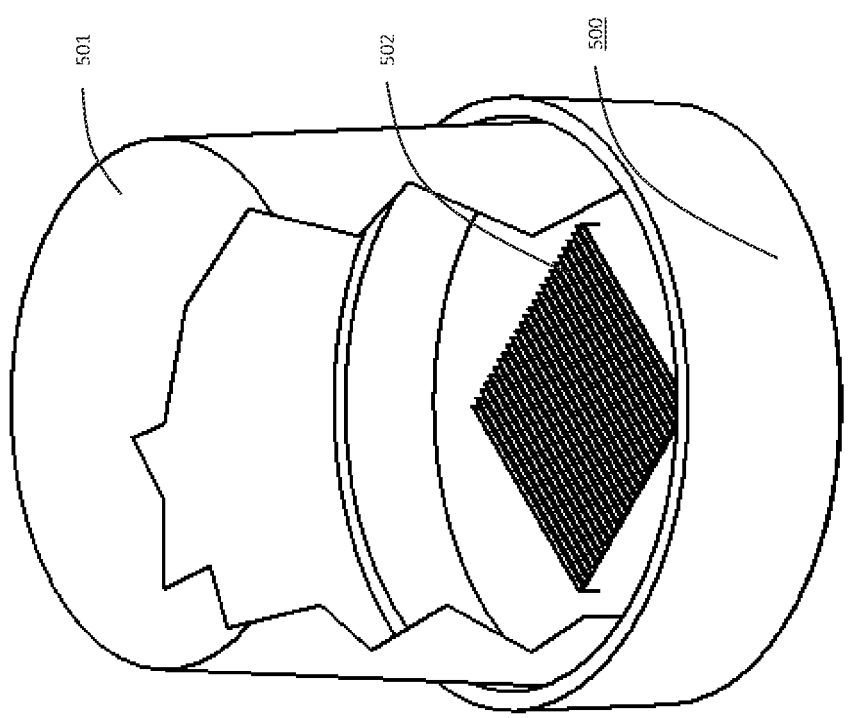
FIG. 2B is an inverted view of the specimen cup (501) for the food sample and container lid (500) that is shown in FIG. 2A. Because the orientation is changed in this view, a *Salmonella* aptamer sensor (502) coupled to the underside of the lid (500) is visible.
Figure 2C:
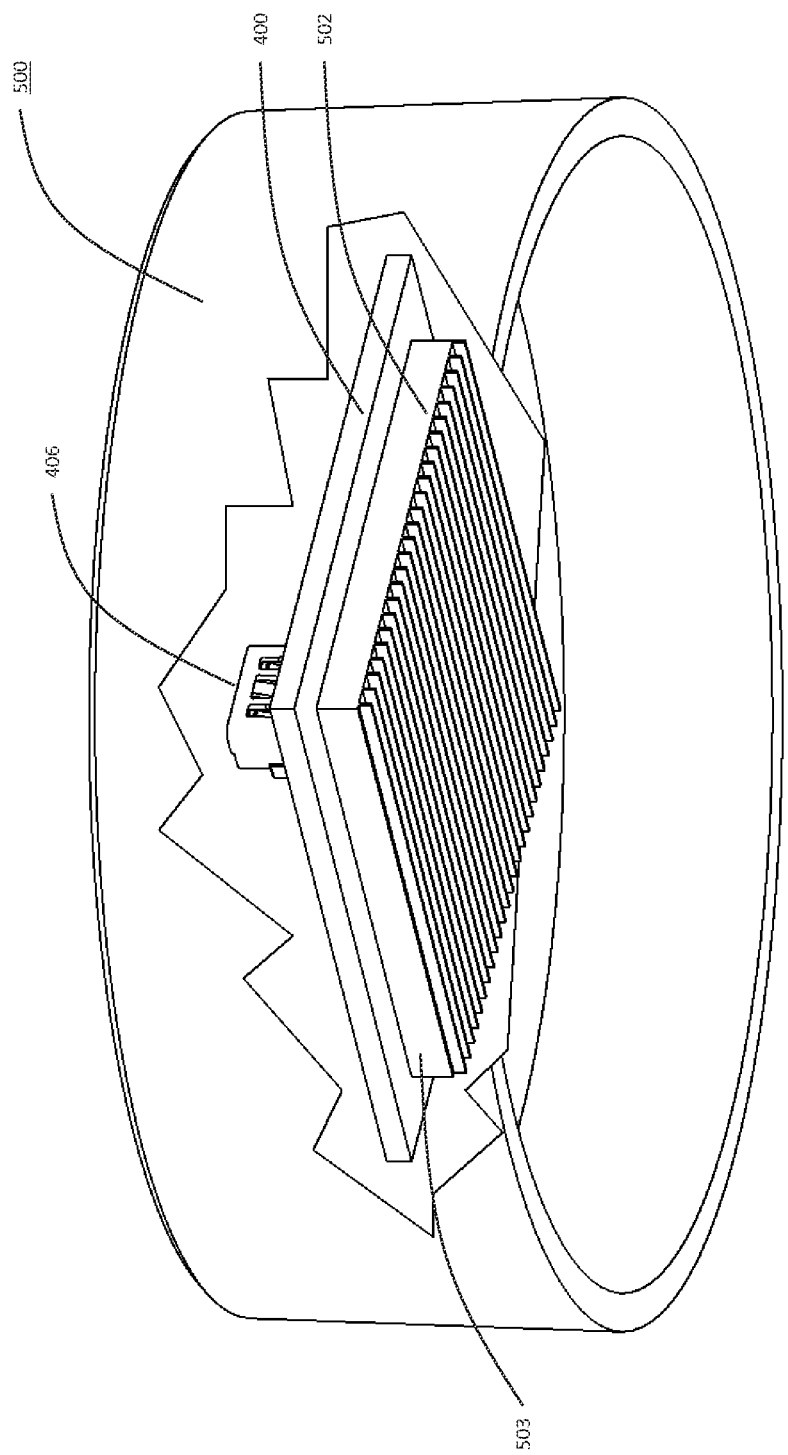
Figure 2D:
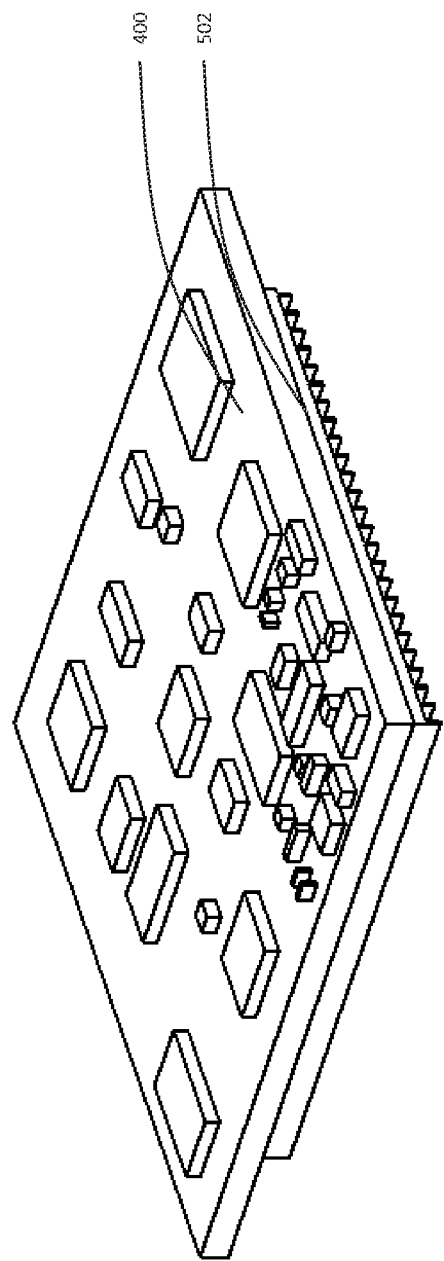

FIG. 2C shows the container lid (500) and its internalized components. The USB connection (406) is coupled to a Printed Circuit Board (PCB) (400) in the lid (500). The USB connection (406) is the data and power coupling point between the specimen cup lid (500) and the base station (600). Coupled to the underside of the PCB (400) in the lid (500) is a *Salmonella* aptamer sensor (502). In an alternative embodiment, the container lid (500) would also include an electric resistance heating coil (not shown). This coil would be capable of heating the contents of the sample cup, thereby decreasing incubation time (described in further detail below).

The *Salmonella* aptamer sensor (502) within the lid (500) must be immersed in a broth during the testing procedure. However, the PCB (400) must be protected from conductive liquid, such as that which is used to cultivate the *Salmonella enterica*. A seal (503) is disposed around the *Salmonella* aptamer sensor (502) which keeps fluids from passing between the aptamer plate (502) and the lid (500), and is utilized to ensure that the PCB (400) is kept dry and functioning during the testing procedure. In an alternative embodiment, an insulation layer or insulation plate (17) seen in FIG. 2E is be placed between the PCB (400) and the aptamer plate sensor (502) in order to protect the PCB (400) from exposure to the substances being tested in the specimen cup (501). It should be expressly understood that the tasks of the seal (503) and the insulation plate (17) may be performed by the same physical component within the device, or may be performed by a plurality of separate components.

The components of the lid assembly are coupled together and to the custom lid (500) to create a tight-fitting assembly by means of epoxy, adhesive, screws, and bolts and the like as readily known by those familiar with the art. The preferred embodiment of the current device would be coupled using primarily plastic fitting clips (not shown) and epoxy, allowing for quick and inexpensive assembly of the invention.

In an alternative embodiment of the invention, a small electric heating element (not shown) is coupled to the inside of the to the lid (500), but not touching the aptamer sensor plate (502), so that it may heat the fluid inside the specimen cup during the testing procedure described in further detail below. This use of the heating element would allow for additional control of the incubation process by heating the contents of the specimen cup (501) to a level where incubation can occur more rapidly. However, because of the additional electrical energy used to power the heating element, it would be necessary to provide larger electro-chemical batteries (615) seen in FIG. 3A that are capable of supporting the requisite power output and duration.

FIG. 2D is a perspective view of the PCB (400) coupled to the *Salmonella* aptamer sensor (502), as described above. The PCB (400) functions as a connection point and communication medium between the aptamer sensor plate (502) best seen in FIG. 2E and the USB data and power interface connection (406) to the cup (501).

FIG. 2E depicts the reverse side of the aptamer sensor base plate (502) shown in FIG. 2D. In FIG. 2E, the aptamer sensor plate (502) comprises an array of electrodes coated with *Salmonella* sensors forming a capacitive array (103). Note that the capacitive array (103) is grooved. In this particular embodiment, no pumping device is needed inside the sample cup (501) to assist the aptamer sensor plate (502) with proper flow.

In an alternative embodiment, a protective top plate (not shown) may be added to the inner-most testing surface of the aptamer sensor plate (502), thereby turning sensor 'grooves' into sensing 'tunnels' that are enclosed on four sides, and open to liquid flow at either end. These sensing tunnels may be either straight or similar to the that of the grooved capacitive array (103) seen in FIG. 2E or may take the form of a 'maze' that winds back and forth over the surface of the aptamer sensing plate (502).

In either of the embodiments presented above, it should be expressly understood that a pumping device (such as a piezoelectric pump, not shown) may be added to improve fluid flow without departing from the original spirit and scope of the invention.

FIG. 3A shows a preferred embodiment of the internal components of the base station unit (600). The wireless antenna (601) is shown again, along with the LCD (602), USB connection (603), and power port (604), as previously described. In addition, a base PCB (610) in the base station (600) is seen, which houses a CPU, flash memory, and other solid state components of the base station (600). The base PCB (610) functions to allow communication between the other electric components of the device. A plurality of batteries (615) are also comprised within the base station (600), providing a power source when the invention is not plugged into an external AC or DC power supply. It is preferred that two C size rechargeable batteries (615) may be used, however other battery power sources or sizes can be used without straying from the scope of the invention. The CPU (not shown) acts as a central control point for collecting and interpreting data from the aptamer sensor plate (502), and for disseminating that data either via the wireless antennae (601) or USB data connection port (603). Data collected is stored on an included flash memory module (not shown) that is built on to the base PCB (610). The construction and utilization of these components is well known to those familiar with the art.

FIG. 3B represents an embodiment of the weatherproof enclosure (700) utilized to protect the base station (600), lid (500) and cup (501) assembly for outdoor use. By using this weatherproof enclosure (700), the assembly may be placed on the outside surface of a shipping container, allowing easy access to the testing device without the hassle of opening the shipping container itself. Additionally, a metal shipping container would effectively act as a Faraday cage (Faraday shield) for any wireless transmission devices that are stored inside the metal shipping container. If the base station (600) were to try to transmit data wirelessly to a central office while inside of a metal shipping container, the transmission would be greatly limited in range or blocked. The weatherproof enclosure (700) is shown articulated by way of a hinge (703), which couples the enclosure lid (701) to the enclosure base (704). A latching mechanism (709) allows the enclosure (700) to be securely closed in a tamperproof manner, and may have a lock-and-key feature (not shown) in some iterations of the invention. In one embodiment, the lid (701) may feature a solar photo-electric cell on its externalized surface. This solar cell may be attached directly to the base station (600) to charge its batteries (615). Alternatively, it may be attached to an additional battery (705) within the enclosure (700) which is then connected to the base station (600) in order to provide additional sources of electrochemical energy. An area (707) defined within the weatherproof enclosure (700) would house the base station (600), lid (500) and cup (501) assembly in such a way that the incubation and testing process may be accomplished entirely inside of the enclosure (700). An external antenna (708) is utilized to boost the signal transmission by a connection from the external antenna (708) to the USB port (603) on the base (600). In one embodiment, the same USB port (603) that transmits data to the externalized antennae (708) from the base station (600) would also power a LCD screen or LCD light (not shown) on the external surface of the enclosure (700). The enclosure (700) is attached to a surface either by the attachment brackets (706), or by a powerful permanent magnet (not shown) attached to the external underside of the enclosure base (704), or by both methods. The device enclosure (700) is shaped so as to allow it to fit in one of the grooves that populate the external surface of a standard 40 foot metal shipping container, and thus allow the standard stacking and use of the container without the enclosure (700) protruding beyond the normal size limits of the container.

FIG. 4A depicts the width (Wcap) (52) of the channels on the capacitive array 103 disposed on the *Salmonella* aptamer sensor plate (502) and the relative distance (Dcap) (51) between the channels of the capacitive array (103). These gaps (51, 52) are important in determining proper capacitance levels for the sensing of the presence of *Salmonella enterica* bacteria (2), as discussed below. The Wcap (52) must be large enough to allow *Salmonella* bacteria (2) to pass through the fluid channel easily without creating a blockage. *Salmonella* bacteria are predominantly motile enterobacteria with diameters around 0.7 to 1.5 μm, lengths from 2 to 5 μm, and flagella which project in all directions. With a Wcap (52) that is approximately 20 times the size of the bacteria being tested, the device avoids blockage of the capacitance channels with debris while creating a known resistance based upon the fluid and material being tested. However, the width (Wcap) (52) of the testing channel must be highly uniform, thereby allowing a predictable capacitance across the channel. To test for *Salmonella* bacteria, the Wcap (52) therefore should be a uniform width of the largest standard measure of the size of *Salmonella enterica* (5 μm) multiplied by a factor of 20, or 100 μm. Widths of greater or less than this amount are specifically envisioned in this invention in the pursuit of greater efficiency of testing, ease of construction, efficiency of power consumption, and other performance advantages. The relative distance (Dcap) (51) is a variable in computing the capacitance of the testing channel, as calculated utilizing the equations 1 through 3 contained herein.

Other variables also affect the capacitance of the testing channel of the capacitive plates (103). The biosensor is based on an electrochemical approach which exploits a label-free detection technique based on capacitance measurements of bio-modified electrode-solution interfaces. Therefore, the total capacitance of the capacitive plates (103), can be model as $C_{cell}$ as shown in Equation 7.

$$C_{cell}=C_{geometry}+C_{electrode/solution} \quad (7)$$

$C_{geometry}$ is the capacitance due to the geometry of the sensor as shown in Equation 1. $C_{electrode/solution}$ is double layer capacitance 106, and 109 shown in FIG. 6, formed between each of the two electrodes and the solution in the electrochemical cell 110. This double layer capacitance can be modeled as shown in Equation 8. $C_{electrode/solution}$ is represented by $C_A$ and $C_B$ in Equations 9 and 10 for electrodes A and B.

$$\frac{1}{C_{electrode/solution}} = \frac{1}{C_{insulator}} + \frac{1}{C_{linker}} + \frac{1}{C_{Macugen}} + \frac{1}{C_{Salmonella\ enterica}} \quad (8)$$

The purpose of the components shown in FIG. 4B and FIG. 4C is to affix the *Salmonella* specific aptamer binding molecule to the surface of the conductive channels that form the capacitive plate (103). FIG. 4B is a magnified conceptual view of an individually immobilized aptamer binding molecule (11). While the two aptamer molecules (number 33 and 45) (Raghavendra Joshi et al.) noted in the description of prior art section above are utilized in the preferred embodiment of this invention, it is specifically envisioned that other oligonucleotide aptamers with high specificity to *Salmonella* bacteria may be utilized as well as or in addition to those disclosed herein. A *Salmonella enterica* bacteria (2) is visible with its binding domain on an outer membrane protein (1). By way of explanation, an aptamer is an oligonucleic acid or peptide molecule that binds to a specific target molecule. An aptamer is specific to a target molecule because the oligonucleic acid or peptide (in the case of the S. Typhirium aptamer, a singular DNA strand molecule) folds in a particular and predictable three dimensional shape due to its chemical structure and composition. However, the aptamer molecules utilized in this invention are 40-mer (sequence length of 40 bases) in size, and add only approximately 10 nm of thickness to the aptamer sensor base-plate. In comparison, *Salmonella enterica* is regularly up to 5 μm in length, making the bacteria several orders of magnitude larger in size than the aptamer binding molecule (11). Therefore, the S. Typhirium aptamer (11) must bind to an outer membrane protein (OMP) of the *Salmonella* bacteria, which is visualized here as the binding domain (1) on the outer membrane protein of the *Salmonella enterica* bacteria (2).

FIG. 4B further shows a conceptualized image of an immobilized *Salmonella enterica* aptamer (11), linked via a linker (Succinic anhydride) (12) to an amino-silanization molecule (13). The amino-silanization molecule (13) is connected to a $SiO_2$ insulator (14), a p-Si substrate (15), and finally to a conductive electrode (16) for the electronics interface. Together, these elements form the smallest working construct of the aptamer sensor plate (502). The insulation plate (17) would be placed directly between the PCB (400) in the lid (500) and the aptamer biosensor plate (502). The insulation plate (17) may be combined with a seal (503) in certain embodiments of the invention.

While FIG. 4B shows a conceptualized individually immobilized *Salmonella enterica* aptamer (11), which represents an immobilized aptamer with high specificity to *Salmonella* enteric. FIG. 4C demonstrates the three-dimensional secondary structure form of aptamer 33 as predicted by Mfold analysis. Many of the components shown in FIG. 4B are also shown in FIG. 4C. The production of aptamer 33 and aptamer 45 are fully disclosed by Raghavendra Joshi et al. (*Selection, characterization, and application of DNA aptamers for the capture and detection of Salmonella enterica serovars*, Molecular and Cellular Probes, Vol. 23, pp. 20-28, 2009), which provide additional structural drawings of aptamers 33 and 45 utilized in this invention.

The creation of a biosensor utilizing individually immobilized aptamer sensor DNA strands (11) is disclosed in full by Hyun-Seung Lee et al., (Electrical detection of VEGFs for cancer diagnoses using anti-vascular endotherial growth factor aptamer-modified Si nanowire FETs, Biosensors and Bioelectronics, Vol. 24, pp 1801-1805, 2009.) The process utilized in the work of Hyun-Seung Lee et al. is followed in this invention, with the substitution of aptamers 33 and 45 (which have *Salmonella enterica* outer membrane protein specificity) for aptamers with VEGF specificity. This substitution will be easily accomplished by one skilled in the art by substituting various aptamers in solution, thereby attaching the 5' end of the aptamer to the sensor plates, allowing the 3' end to float in order to binding to the *Salmonella enterica* bacteria target. Utilizing the techniques disclosed by Hyung-Seung Lee et al., it is possible to immobilize a plurality of DNA based aptamer sequences which are interchange with a sensor plate.

The following is a brief summary of the methods that are fully elucidated in the references above. Succinctly put, anti-*Salmonella* aptamers are immobilized to the surface of the conductive electrodes (16) with a p Si substrate layer (15) shown in FIG. 4A and $SiO_2$ insulator (14) through a self-assembled monolayer (SAM) process. Each aptamer (11) utilizes an individual copy of the amino-silanization molecule (13) and linker (Succinic anhydride) (12) to ultimately attach the aptamer molecule (11). These components are constructed and assembled in the manufacturing process of the described invention, and layered to create the biosensor plates utilized to detect the presence of *Salmonella enterica* bacterial growth.

Turning to FIG. 5, a cross section of the capacitive array (103) is shown with a schematic representation of the electronic detection module. The capacitive array (103) comprises a substrate (15) that is configured to allow fluid flow over the surfaces in the capacitive array 103 lined with immobilized aptamer strands (11).

The incubation broth (e.g. BHI broth) flows into the capacitive array (103) via gravity and any natural flows produced by movement as the base station (600) is in transit. In an alternative embodiment, a small electric pump (e.g. a piezoelectric pump, not shown) is used to increase flow of liquid over the capacitive array (103). The electrode plate array assembly (100) comprises of an array of electrodes (300) coded with aptamer strands (11) in immobilized layers over the capacitive plates (103). The electrodes (300) are designed in a 'comb' pattern in order to maximize the sensor surface area in a small volume while also maximizing free flow of liquid. The lectrode plate array assembly (100) is interfaced with a capacitance detector circuit (200). The detector circuit (200) includes an Operational Amplifier buffer (201); a current-to-voltage amplifier (202), comprising a resistor (204); and an Op Amp integration circuit (203), comprising a resistor (205) and a capacitor (206). The values of the resistor (205), and capacitor (206), are matched approximately to the resistor (204) and capacitance of the substrate (100), respectively, so that the output signal (210) is approximately the same as input square wave (207). The half period of the input square wave (207), should be significantly larger than the RC constant formed by the resistor (204) and the substrate (100), so that the Op Amp (202) has enough time to discharge the sharp transitions caused by the square wave (207). As the capacitance of capacitive array (103) increases with arrival of target analytes (2), the amplitude of output signal (210) increases proportionally. The detail mechanism behind this measurement technique is elaborated further in the definitions section above.

Figure 2E:
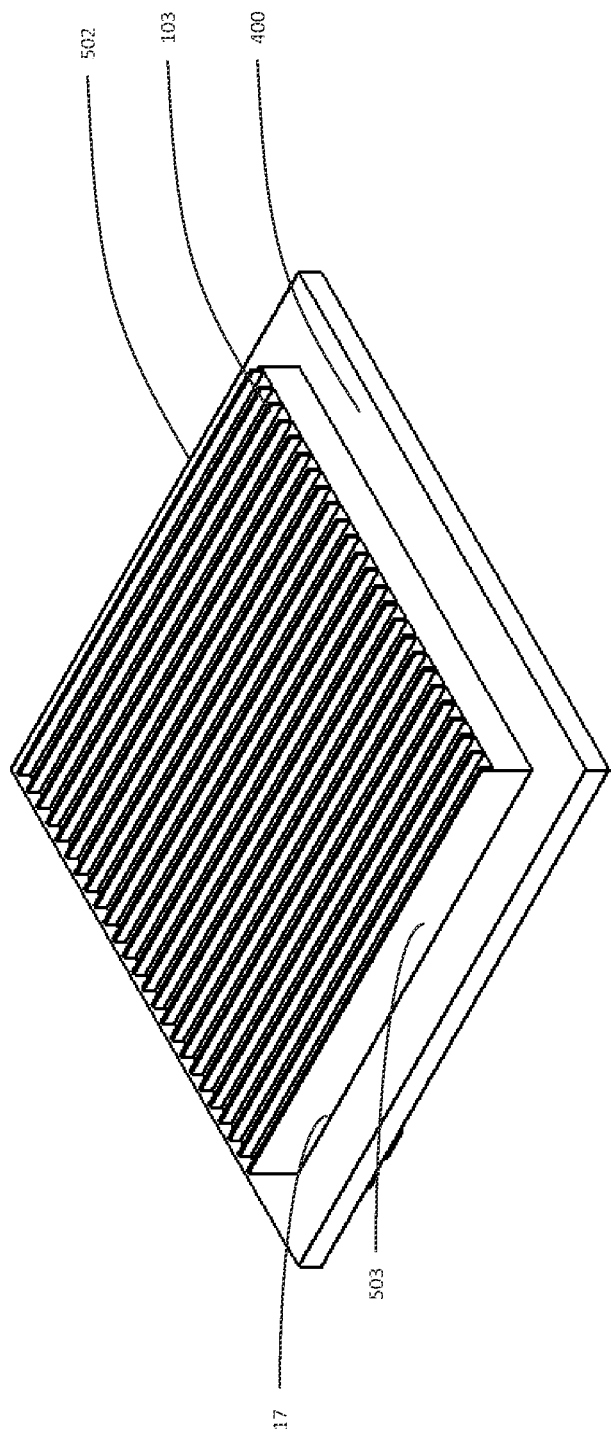
Figure 3A:
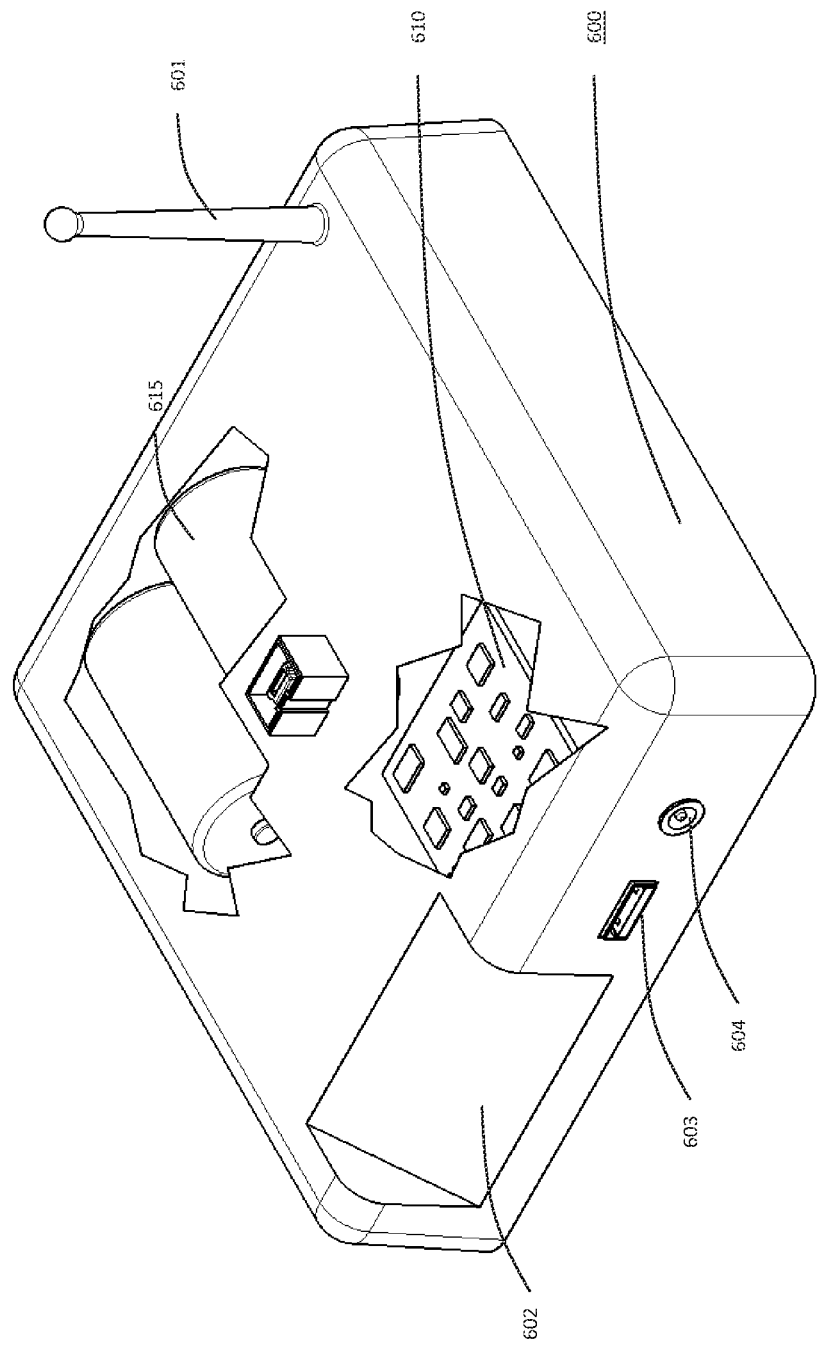
Figure 4A:
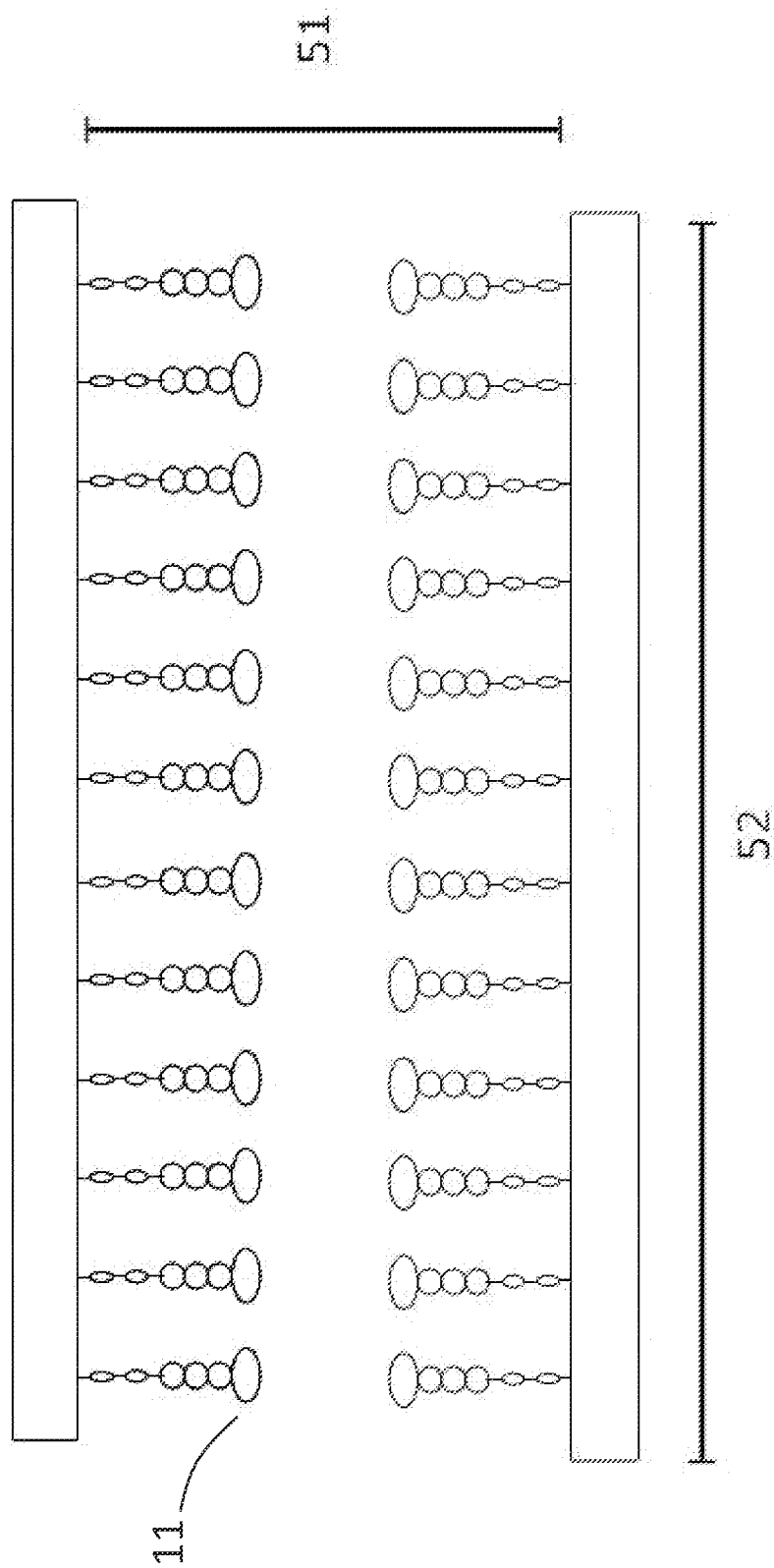
Figure 4B:
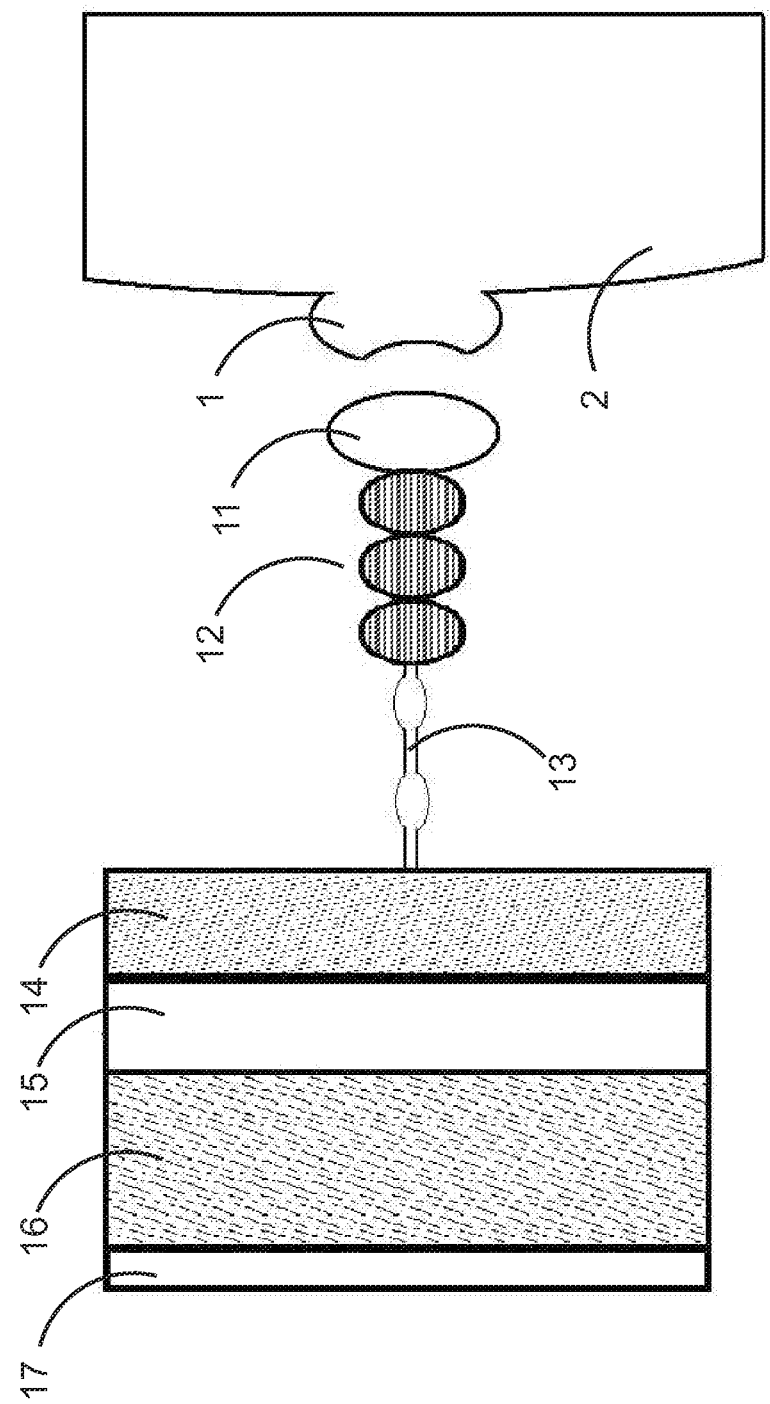
Figure 4C:
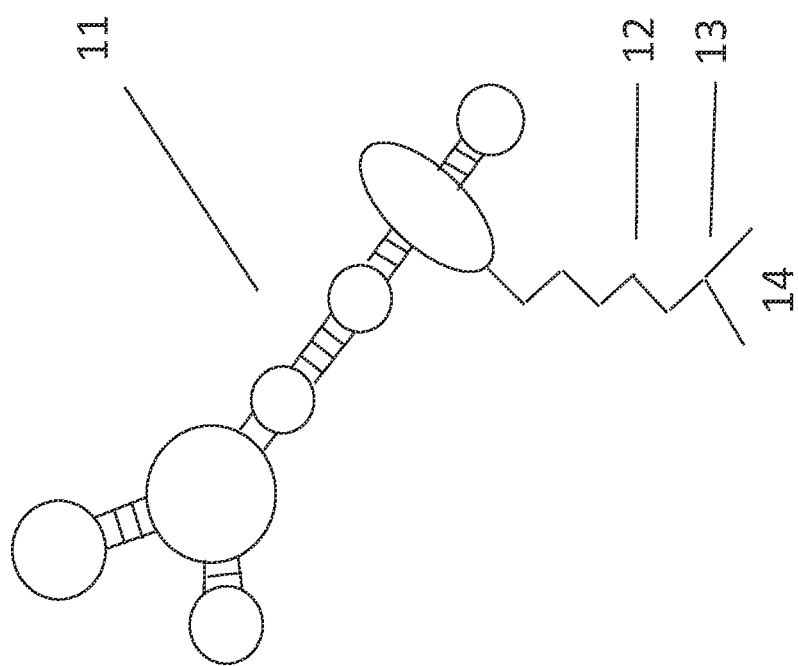
Figure 5:
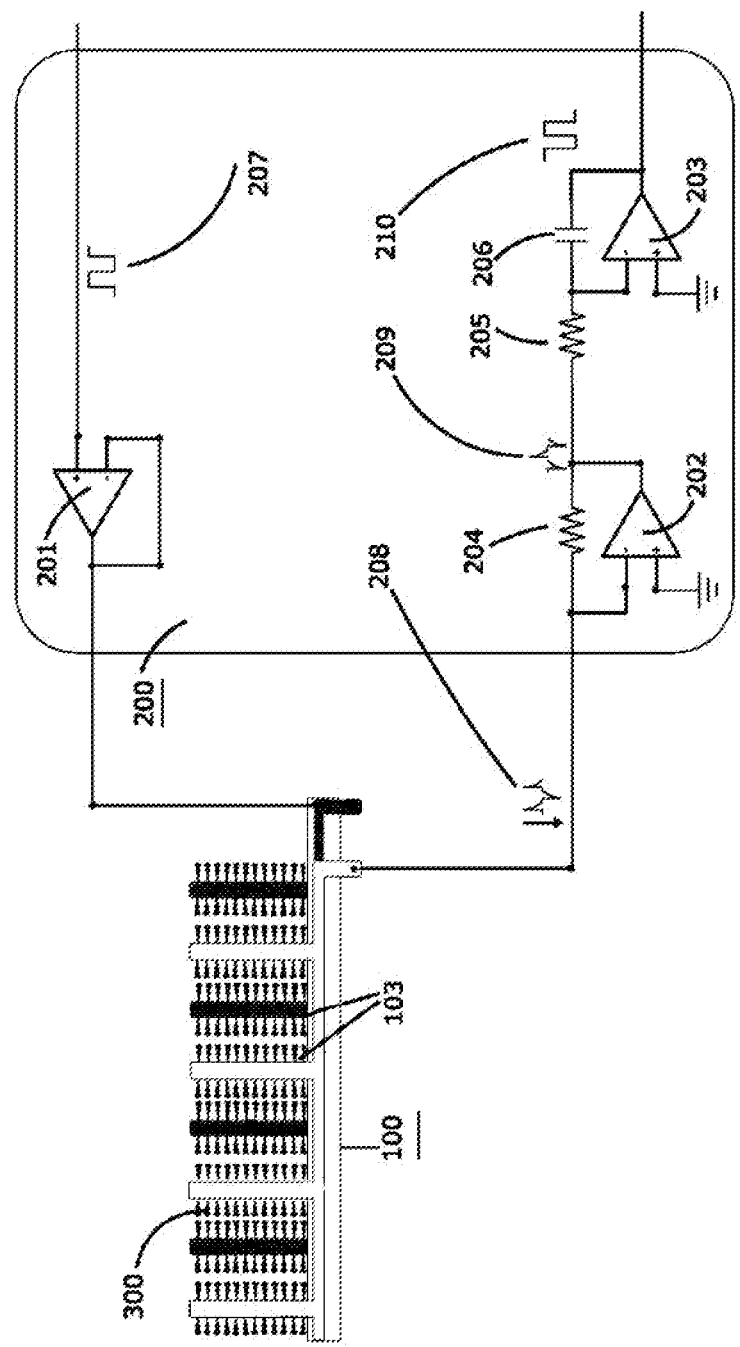
Figure 6:
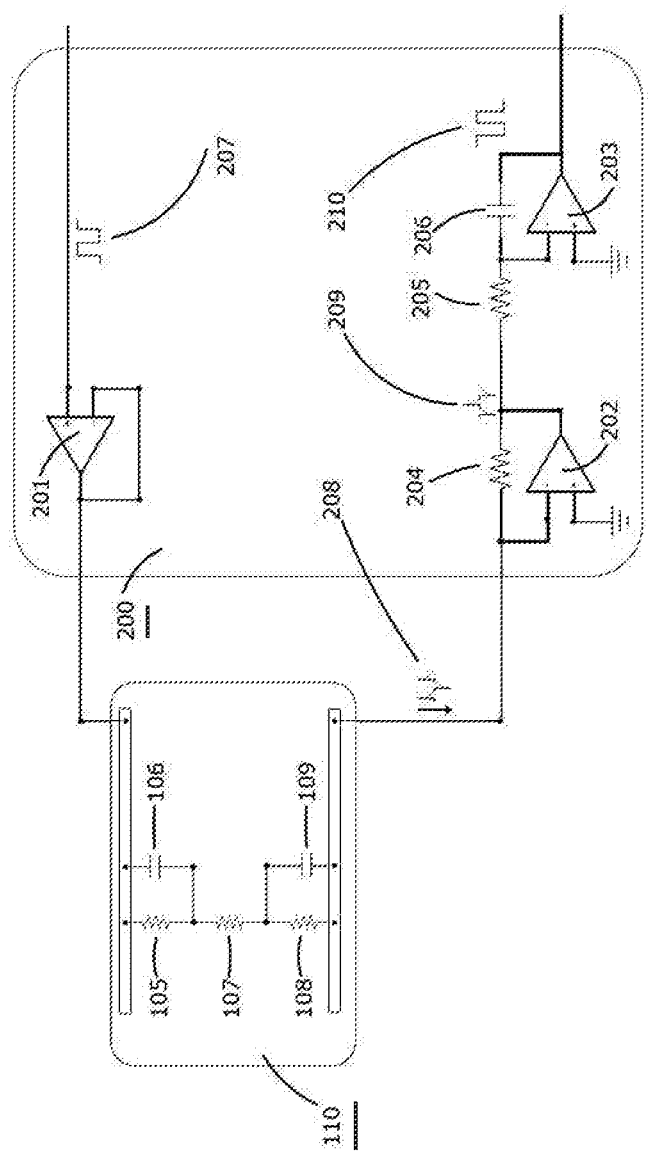

FIG. 6 is a schematic representation of the preferred embodiment of the invention depicting an equivalent electrical circuit of the capacitor array (103) shown in FIG. 2E. and is also an alternate embodiment of the detector circuit shown in FIG. 5. Utilizing this capacitor array (103) and detector circuit (200), changes in capacitance between the aptamer sensor electrodes (300) is utilized to detect the presence of Salmonella enterica bacteria (2). In this representation of the capacitive aptamer-based Salmonella enterica sensor plate (502), the capacitor plates coated with Salmonella-specific aptamer molecules (103)) are identified by their respective effective geometrical terms Gx (300). The values of the effective geometrical terms Gx (300) are chosen so that the change in capacitance can be effectively measured utilizing the boundary conditions for the fluid channels in the capacitive array (103). These boundary conditions can be measured as the selection of the dimensions $d_{cap}$ (51), the distance between the sensor plates in calculating the capacitance value, and $W_{cap}$ (52), the width of the sensor plates used to calculate the capacitance value. These values are defined by providing an unrestricted circulation flow of fluid through the sensor plate (502), specifically through the channels created by the capacitive array (103) of electrodes (103) coded with Salmonella aptamer sensors (11). The $d_{cap}$ (51) and $W_{cap}$ (52) variables and their utility are best seen in FIG. 4A.

FIG. 6 goes on to show an Op Amp buffer (201) utilized to increase the input impedance of a detector circuit (200), and ensure a near perfect square wave from an input signal (207). A current signal (208), which is proportional to the amount of hybridization of the analytes with the capture reagents, is detected at the output of circuit (200) due to its impedance. An active amplifier (202), transforms the current signal (208), into a voltage signal (209), whose area under the curve is proportional to the hybridization.

Further shown in FIG. 6 is the circuit schematic, noted by reference designator (110), which comprises a resistance of the interface between electrode A and test sample solution (RA) (105), a double-layer capacitance between electrode A and test sample solution (CA) (106), the resistance (RS) (107) of the test sample solution within the sensor body (100), a resistance of electrode B/solution interface (RB) (108), and a double-layer capacitance of electrode B/solution interface (CB) (109). The capacitive array (103) disposed on the sensor plate (502), is interfaced with the capacitive detector circuit (200). The Op Amp buffer (201) increases the input impedance of the detector circuit (200), and ensures a near perfect square wave from the input signal (207). A current signal (208), which is proportional to the amount of hybridization of the analytes with the capture reagents, is detected at the output of detector circuit (110) by the active amplifier (202). The active amplifier (202) transforms the current signal (208) into a voltage signal (209), whose area under the curve is proportional to the hybridization. Because capacitance of the capacitive array (103) changes in the presence of Salmonella enterica bacteria (2), by interpreting the voltage signal utilizing the circuit schematic presented allows the device to test for the presence and level of Salmonella enterica bacteria.

Figure 7:
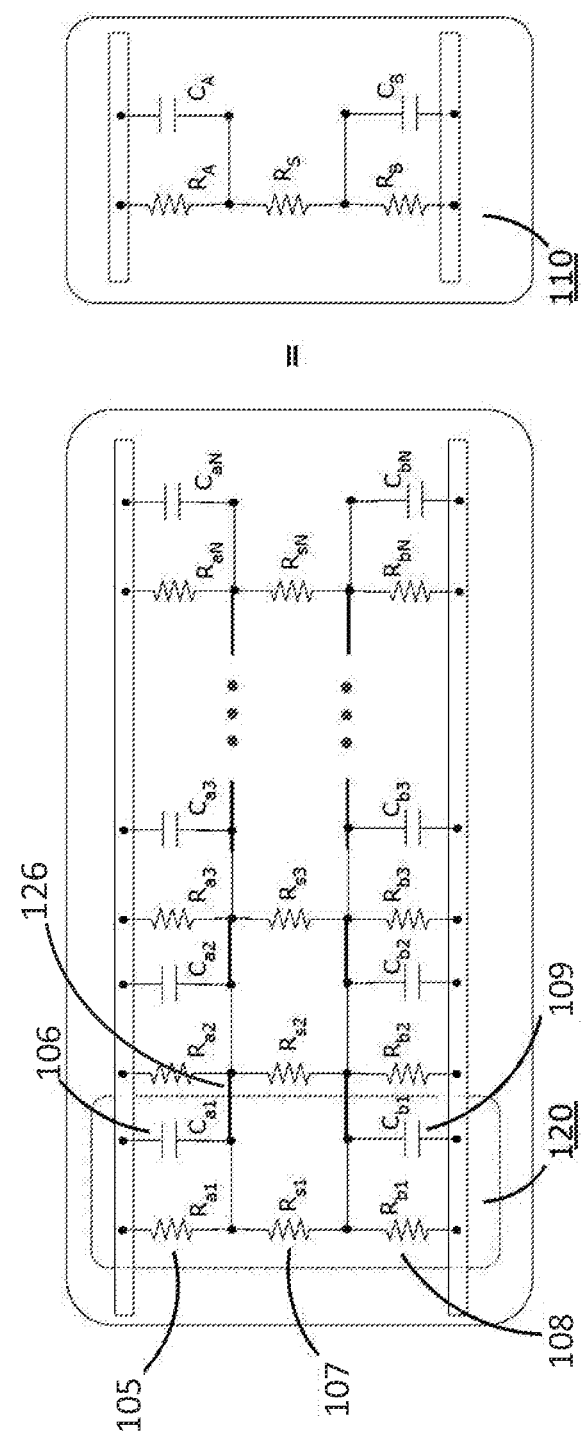

FIG. 7 shows an equivalent circuit to that of the detector circuit (110) of the Salmonella biosensor and how the circuit can be decomposed to model for each pair of capacitive plates (300) in the capacitive array (103). Each pair of capacitive plates (300) forms an electrode-electrolyte interface with the solution which can be represented with an equivalent circuit (120). Because the solution medium is dynamic, the circuit for each plate pair (300) is shorted at the electrode and solution interface (126). Note that the detector circuit (110) appears in both FIG. 6 and FIG. 7. Several identical components are therefore shown in FIG. 6 and FIG. 7, with identical components listed by identical number identifiers in the figures. The following parts referenced by different numbers in FIG. 6 and FIG. 7 are described in unison for clarity. The interface between electrode A and test sample solution (RA) (105); a resistance of the interface between electrode A and test sample solution (RA) (105); a double-layer capacitance between electrode A and test sample solution (CA) (106); a resistance (RS) (107) of the test sample solution within the sensor body (100); a resistance of electrode B/solution interface (RB) (108); and a double-layer capacitance of electrode B/solution interface (CB) (109). By using the schematic shown, the aptamer biosensor capacitance circuit is able to regularize inflow and outflow of voltage, thereby testing the capacitance at the resistance (107) of the liquid medium between capacitance plates (300). This result is utilized to determine the density of the liquid present, and interpret this data in order to determine the presence of Salmonella enterica bacteria (2) present in solution.

Thus, the equivalent circuit of the entire sensor can be written as the combined circuits of each plate pair, which is electrically in parallel to its neighbor pair. Equations 9-13 allow the parameters of the detector circuit (110) be derived from the parameters of each plate pair (120).

$$C_A = C_{a1} \parallel C_{a2} \parallel \ldots \parallel C_{aN} = \sum_N C_{ai} \qquad (9)$$

$$C_B = C_{b1} \parallel C_{b2} \parallel \ldots \parallel C_{bN} = \sum_N C_{bi} \qquad (10)$$

$$R_A = R_{a1} \| R_{a2} \| \ldots \| R_{aN} = \frac{1}{\sum_N \frac{1}{R_{ai}}} \quad (11)$$

$$R_B = R_{b1} \| R_{b2} \| \ldots \| R_{bN} = \frac{1}{\sum_N \frac{1}{R_{bi}}} \quad (12)$$

$$R_S = R_{s1} \| R_{s2} \| \ldots \| R_{sN} = \frac{1}{\sum_N \frac{1}{R_{ci}}} \quad (13)$$

Figure 8:
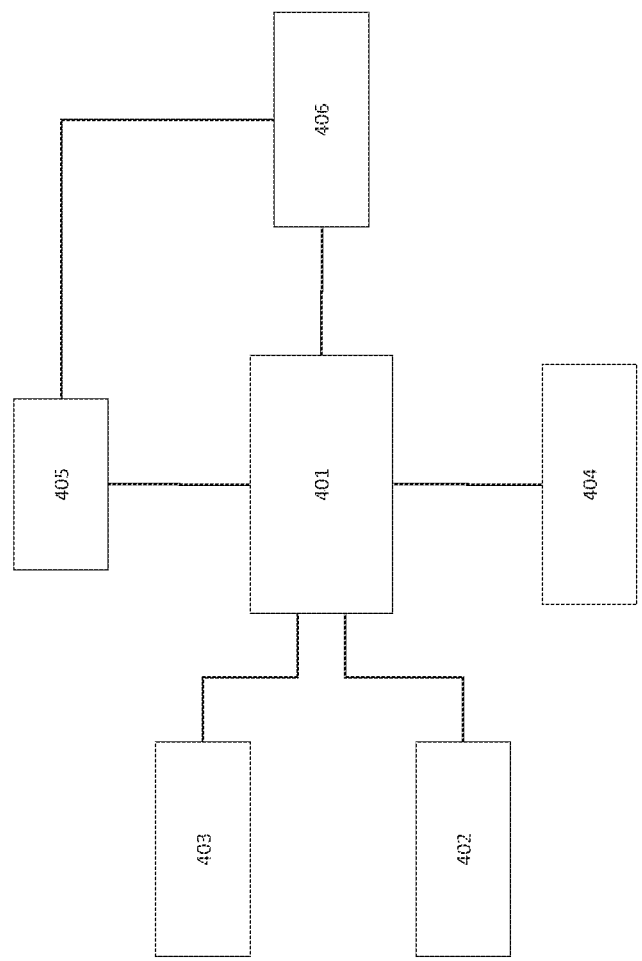

FIG. 8 is a schematic block diagram of a temperature sensor (403) disposed on the PCB (400) coupled within the lid (500). A microcontroller (401) in the lid (500) acts as the master control by reading the *Salmonella* aptamer sensor plate (502) and the temperature sensor (403) and then writing this data to a memory present on the base PCB (610) in the base station (600). An optional circulation pump (404) is also controlled by the microcontroller (401), while the power supply (405) for the cup (501) is provided by means of USB communication from the lid USB port (406) to the base station (600).

Figure 9:
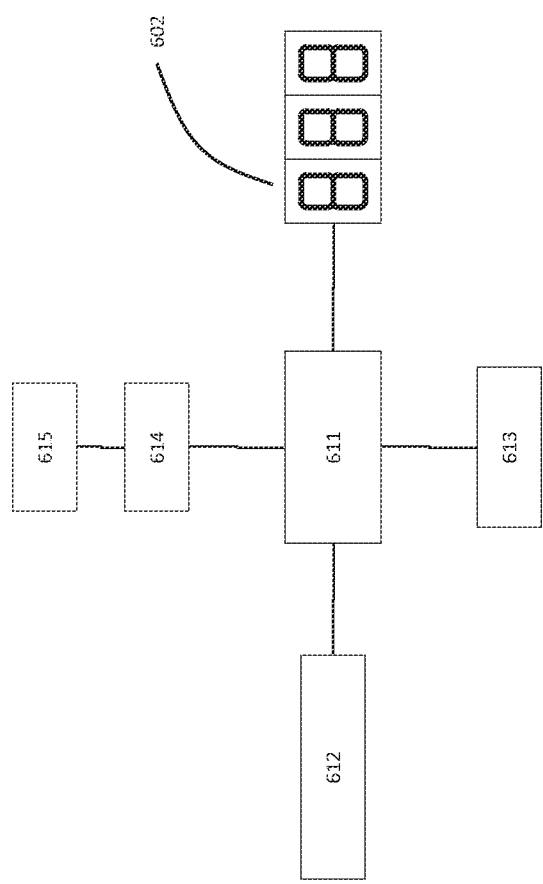

FIG. 9 is a schematic block diagram of the computations performed by a Central Processing Unit (CPU) (611) on the base PCB (610). The CPU (611) in the base station (600) communicates and commands all aspects of the base PCB (610). Wireless communication via the antenna (601) to an external receiver (612) allows communication between the aptamer based *salmonella* detection system and a central control location such as an external computer for data collection. The lid USB communication (613) to the lid (500) provides the input from the sample analysis taking place in the cup (501). Further, a power supply (614) for the base station (600) is provided via batteries (615) under normal operation. The use of the antenna (601) and batteries (615) allows cordless and wireless use of the device. Finally, the CPU (611) also dictates what input from the sensor plate (502), temperature, capacitance, etc. is displayed on the display 602.

The invention described herein is designed to be highly automated so as to allow minimal training to be needed in order to carry out the examination. For example the device can be installed on the container that is transporting the goods to be tested.

Figure 1:
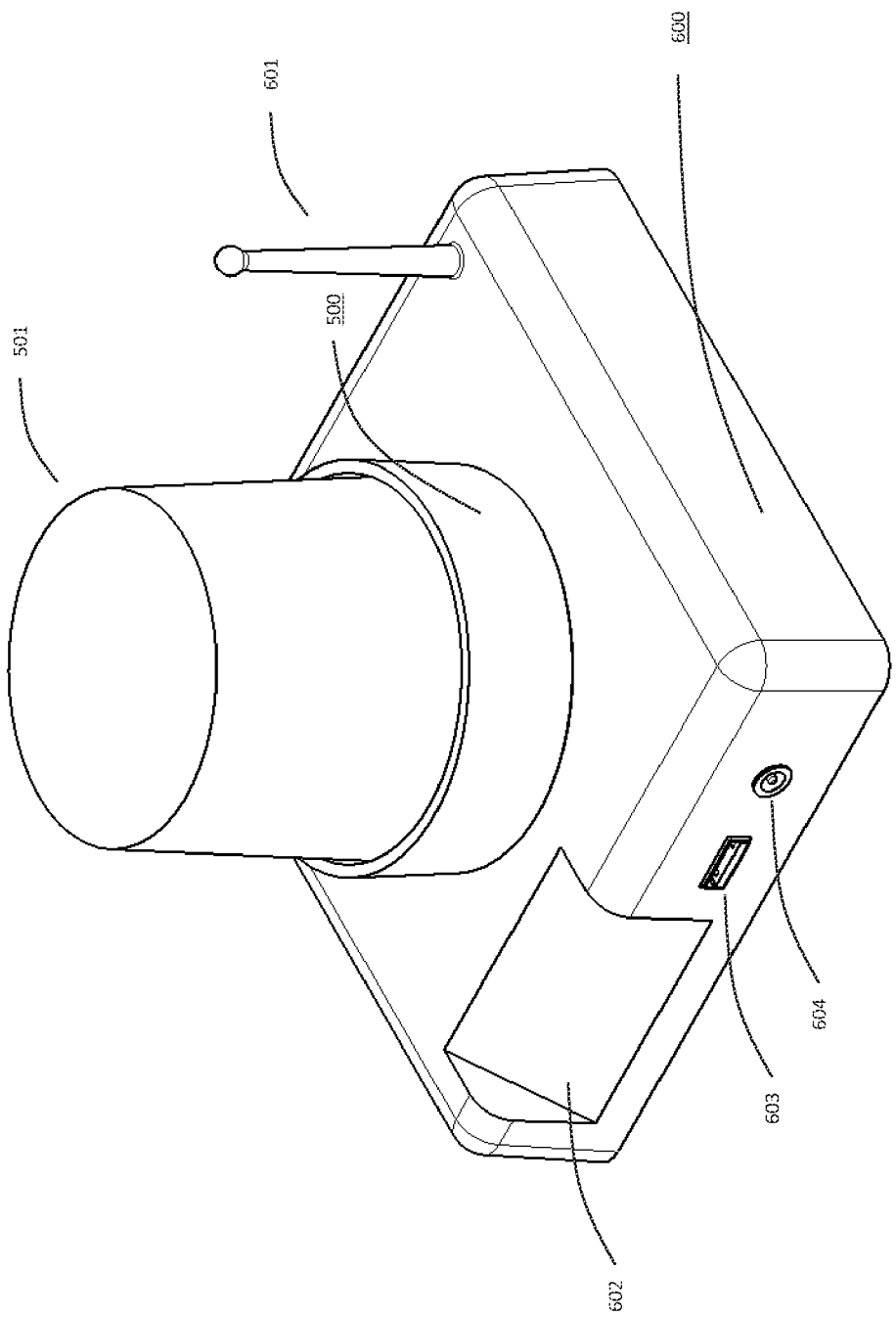

To prepare a testing cycle, broth will be added in a set amount to the cup (501), allowing enough room for addition of a sample of the food. The broth utilized for incubation will be of a standard and currently commercially available variety, such as BHI broth. An additional enrichment media may be added to increase the speed of incubation. The food sample is then added to the specimen cup (501) utilizing sterilized instruments as needed. Next, the lid detection device (500) is prepared for use by pulling a plastic tabbed cover (not shown) from the aptamer sensing plate (502), if present. Subsequently, the lid (500) is placed firmly on the specimen cup (501), and the closed specimen cup is shaken vigorously for approximately 30 seconds. This process thoroughly mixes the broth and food sample. The closed specimen cup is then turned upside down and placed into the base station (600) as seen in FIG. 1, and in doing so, the USB connection between the aptamer sensor lid (500) and the base station (600) is established.

Once the food sample has been added to the broth, and the specimen cup has been placed on the base station, the sample is allowed to incubate in order to cultivate the increase the presence of *Salmonella* bacteria (2) to a readily testable level.

The device is utilized first by taking a pre-set amount of commercially available broth (such as BHI broth) that is appropriate for the standard commercially available specimen cup (501) size being used. Next, a small sample of the item to be tested (e.g. a piece of chicken) is placed into the cup using commercially available sterilized tablespoons, scissors, forceps, knives, glass stirring rods, pipettes, petri dishes, test tubes, bent glass rods ("hockey sticks") as needed. Next, the specimen cup container lid (500) with the aptamer biosensor capacitive array (103) built in is placed securely on the top of the specimen cup (501), and the cup (501) is shaken vigorously for a short period of time to mix the contents and broth. Finally, the cup (501) is placed top-side-down onto the base station unit (600), with the USB ports (406, 603) in the lid (500) and the base station (600) securely connected. If an externalized weatherproof container (700) is used to house the device during the testing phase, the base station (600) with its properly connected lid (500) and specimen cup (501) are then placed inside of the weatherproof container (700).

Alternatively, the device could be stored inside of a shipping container with the food sample, in the cab area with the driver of a truck, or in a centralized office for the repository of such testing devices at a port. The preferred embodiment would keep the sample and the goods being shipped physically close at all times, allowing further testing of the sample at the point of destination.

The remainder of the testing process is accomplished without the aid of human hands. Following the preparation of the sample and proper storage of device as described above, the base station (600) begins the automated process by which it tests for the presence of *Salmonella enterica* (2). From this point onward in the procedure, the device performs functions without physical external input. This process begins by allowing time for the incubation of the *Salmonella* sample (2) in broth to reach detectable levels. The amount of incubation time is determined by the ambient temperature. A temperature sensor (403) is built into the PCB (400) in the lid (500), thereby allowing accurate measurement of the temperature in the sample. Based upon calculations found in prior art (Vijay K. Juneja et al., *Modeling the effect of temperature on growth of Salmonella in chicken*, Food Microbiology, Vol. 24, pp. 328-335, 2007), if the temperature of an incubation cycle is known, the amount of time needed for a proper incubation cycle can be determined with great accuracy. In this way it is not necessary to artificially control the temperature of the incubation of the *Salmonella enterica* bacteria (2) during testing.

Generally, higher incubation temperatures lead to shorter incubation times. If artificial temperature increases for the purpose of decreasing incubation time is desired or needed, the optional heating element (not shown) in the lid (500) would be utilized.

Once the proper incubation period has been completed, the biochemical aptamer-based biosensor configuration detailed in FIG. 4B is utilized to measure for the presence and quantity of *Salmonella enterica* bacteria (2). The device utilizes aptamer binding DNA strands (11) immobilized onto a capacitive array (103) to accomplish the testing process. Immobilized aptamers (11) have a high affinity and specificity for binding to the outer membrane proteins (OMPs) (1) of the *Salmonella* bacteria (2). Capacitance plates (300) form a 'comb' like structure to create a sensor array (103) seen in FIG. 5, where the two facing sides of the comb 'teeth' create the positive and negative interfaces of the capacitance circuit. When a source being sampled contains *Salmonella enterica* bacteria (2), the immobilized aptamer (11) binds to the *Salmonella* bacteria (2) and traps it between the capacitance plates (300). The capacitance between plates (300) is measured. Because the presence of *Salmonella enterica* bacteria (2) changes the capacitance between the plates (300), measuring the capacitance allows for detection of the level *Salmonella* bacteria (2) in the sample. This method creates an electrochemical biosensor that is capable of testing for the presence of *Salmonella enterica* bacteria (2) from a given sample.

Once the testing procedure has been completed, the results are analyzed, interpreted, and transmitted by the base station (600). Results can be wirelessly transmitted at any Wi-Fi access point via the antennae (601), such as those present in warehouses and at weigh stations. After the testing procedure is accomplished, the cup (501) and lid (500) are disposed of, and the base station (600) is utilized with a new cup (501) and lid (500).

Standard off-the-shelf components are utilized whenever possible for the purpose of diminishing the cost of the device, while also maintaining the high level of quality and versatility that can be garnered by utilizing standardized parts.

Programming of the device can be accomplished via the USB connection (603) on the base station (600). It may also be accomplished wirelessly, thereby allowing troubleshooting of multiple devices from a central office. The base (600) of the device utilizes a Liquid Crystal Display (LCD) screen (602) to output visually the state and results of the testing procedure without the need to connect to a standard personal computer. The device is programmed at a central location so that the field use of the device is as simplified as possible, and also to avoid tampering with the device via manipulation of the controls. The device may be powered by an electrical source of any kind, including batteries (615), the DC current from a truck or car or externalized battery (705) attached via the power charging port (604), or by AC current from a wall socket, or other source to the charging port (604).

Finally, the device allows for previously unavailable simplified collection of data on food spoilage. Because the device runs at all times, and utilizes a real-time clock along with a temperature sensor, the device is capable of recording conditions within the sample at all times during the transit of the device. This kind of information has not been available previously, and will allow for the designing of higher accuracy predictions in regards to food spoilage, based upon time and temperature conditions.

In summary, the disclosed invention allows for highly automated, accurate testing for *Salmonella enterica* bacteria (2) in food sources during transit, accomplished by lightly trained personnel, but also providing high accuracy and at a reasonable cost. Further, the device will collect information on *Salmonella enterica* (2) over time and record this information, allowing for greater accuracy and more dependable results.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

We claim:

1. An apparatus for detecting *Salmonella enterica* bacteria using an electrochemical aptamer-based sensor array comprising:
 a sensor base plate;
 a capacitive array disposed on the sensor base plate in a plurality of grooved channels;
 a plurality of aptamer molecules disposed within the capacitive array, each of the plurality of aptamer molecules capable of binding to an indicator protein on an outer membrane of the *Salmonella enterica*, and wherein each aptamer molecule is immobilized to the capacitive array utilizing the Self-Assembled Monolayer (SAM) method;
 a printed circuit board coupled to the capacitive array, the printed circuit board comprising means of interfacing and controlling the capacitive array, and wherein the printed circuit board and capacitive array are powered directly or indirectly to an independent power supply through a USB connection;
a resistive heating element coupled to and powered by the printed circuit board;
a delivery system for delivering a fluid for analysis to the capacitive array, wherein the delivery system comprises a piezoelectric pump coupled to the sensor base plate to ensure proper liquid flow over the capacitive array; and
a weatherproof enclosure sized and configured to house the apparatus, wherein the enclosure comprises a plurality of attachment brackets comprising means for allowing the enclosure to be coupled to the external surface of a shipping container,
wherein the plurality of attachment brackets of the enclosure further comprises means for the enclosure to fit within a pair of extended corrugations on the external surface of a standard shipping container, the enclosure comprising a profile less than that of the extended corrugations on the external surface of the standard shipping container.

2. The apparatus of claim 1 where the capacitive array disposed on the sensor plate is configured in a plurality of tunnels that are enclosed on four sides and open to liquid flow at either end.

3. The apparatus of claim 1 wherein each of the plurality of aptamer molecules further comprises:
a linker molecule acting as an immobilizer coupled to the aptamer molecule;
an amino-silanization layer coupled to the linker molecule; and
a SiO2 insulator coupled to the amino-silanization layer and to the capacitive array.

4. The apparatus of claim 1 wherein the means of interfacing and controlling the capacitive array by the printed circuit board further comprises means for detecting the change in capacitance in the capacitive array due to the presence of *Salmonella enterica* bacteria between a pair of the plurality of grooved channels.

5. The apparatus of claim 1 where the delivery system comprises means for providing an unrestricted circulation flow of the fluid through the capacitive array.

6. An apparatus for testing for *Salmonella enterica* bacteria comprising:
a specimen cup;
a lid comprising an aptamer-based sensor array, the lid being removeably coupled to the specimen cup;
a base station comprising means for interfacing with the lid, wherein the base station comprises:
an electrochemical battery array;
a printed circuit board comprising a CPU and a flash memory;
a liquid crystal display screen;
a USB port comprising means for power acquisition and data communication:
a power port comprising means for connecting to an AC or DC power source ranging from 110 to 240 volts; and
a wireless antenna comprising means for communicating in standard Wi-Fi and cellular phone frequencies;
a weatherproof enclosure sized and configured to house the apparatus including the base station, the lid, and the specimen cup, wherein the enclosure comprises:
a solar photo-electric cell;
an electrochemical battery coupled to the base station and comprising means for collecting power from the solar photo-electric cell and delivering that power to the base station;
an external booster antenna coupled to the base station via the USB port on the base station; and
a plurality of attachment brackets comprising means for allowing the enclosure to be coupled to the external surface of a shipping container; and
a strong permanent magnet coupled to the backside of the enclosure and comprising means for semi-permanent attachment of the enclosure to ferrous surfaces,
wherein the plurality of attachment brackets of the enclosure further comprises means for the enclosure to fit within a pair of extended corrugations on the external surface of a standard shipping container, the enclosure comprising a profile less than that of the extended corrugations on the external surface of the standard shipping container.

7. The apparatus of claim 6 wherein the base station comprising means for interfacing with the lid further comprises the base station being removeably coupled to the aptamer-based sensor array within the lid by means of a USB connection.

* * * * *